(12) United States Patent
Hartmann et al.

(10) Patent No.: US 10,113,995 B2
(45) Date of Patent: Oct. 30, 2018

(54) MULTI-POSITION, MICRO-FLUIDIC VALVE ASSEMBLY WITH MULTIPLE RADIAL GROOVES TO ENABLE INDIVIDUAL OR COMBINED FLOWS

(71) Applicant: IDEX Health & Science LLC, Northbrook, IL (US)

(72) Inventors: Daniel M. Hartmann, Middleboro, MA (US); Darren Lewis, Oak Harbor, WA (US); Jon Nichols, Rohnert Park, CA (US); Jim Smyth, Rohnert Park, CA (US)

(73) Assignee: IDEX Health & Science LLC, Northbrook, IL (US)

(*) Notice: Subject to any disclaimer, the term of this patent is extended or adjusted under 35 U.S.C. 154(b) by 96 days.

(21) Appl. No.: 14/943,962

(22) Filed: Nov. 17, 2015

(65) Prior Publication Data

US 2016/0139094 A1    May 19, 2016

Related U.S. Application Data

(60) Provisional application No. 62/081,256, filed on Nov. 18, 2014.

(51) Int. Cl.
| | |
|---|---|
| *F16K 11/074* | (2006.01) |
| *G01N 30/20* | (2006.01) |
| *F16K 99/00* | (2006.01) |
| *G01N 30/02* | (2006.01) |

(52) U.S. Cl.
CPC ......... *G01N 30/20* (2013.01); *F16K 99/0013* (2013.01); *F16K 99/0028* (2013.01); *F16K 99/0042* (2013.01); *F16K 2099/0084* (2013.01); *G01N 2030/027* (2013.01); *G01N 2030/202* (2013.01)

(58) Field of Classification Search
CPC .............. G01N 30/20; G01N 2030/202; F16K 11/074; F16K 11/0743; Y10T 137/86863
USPC ................. 137/250, 625.11, 625.15, 625.46; 73/61.56, 863.73
See application file for complete search history.

(56) References Cited

U.S. PATENT DOCUMENTS

| | | | | |
|---|---|---|---|---|
| 4,625,569 A | * | 12/1986 | Toei .................. | G01N 35/1097 73/863.72 |
| 5,650,577 A | * | 7/1997 | Nagai ...................... | F16K 3/36 436/179 |
| 6,012,488 A | * | 1/2000 | Nichols ............... | F16K 11/0743 137/625.11 |

(Continued)

*Primary Examiner* — Reinaldo Sanchez-Medina
(74) *Attorney, Agent, or Firm* — Beyer Law Group LLP

(57) ABSTRACT

A rotary shear valve having a rotor device and a stator device both with planar faces. The stator face includes a central port located at a common rotational axis, a second port radially spaced a radius R1 from the central port, and a third port spaced at radius R2. The second and third ports are in general linear alignment with the central port. The rotor face includes a first rotor groove extending radially outward from the common rotational axis to a position at radius R2 from the central port. The rotor device is rotatably mounted to the stator device for rotation thereof about the axis, providing fluid-tight, selective relative rotation therebetween between two or more discrete rotor positions. When in a discrete first rotor position, the first rotor groove is oriented in radial alignment with, and fluidly connects, the central port and the second port with the third port.

11 Claims, 17 Drawing Sheets

(56) References Cited

U.S. PATENT DOCUMENTS

| | | | | |
|---|---|---|---|---|
| 6,382,035 B1* | 5/2002 | Nichols | .................. | G01N 30/20 |
| | | | | 73/863.72 |
| 6,852,291 B1* | 2/2005 | Johnson | ............... | B01J 19/0046 |
| | | | | 137/597 |
| 8,960,231 B2* | 2/2015 | Picha | ..................... | G01N 30/20 |
| | | | | 137/625.46 |
| 2003/0098076 A1* | 5/2003 | Nichols | ................ | F16K 11/074 |
| | | | | 137/625.46 |
| 2009/0320925 A1* | 12/2009 | Nichols | ..................... | F16K 3/08 |
| | | | | 137/1 |
| 2011/0067770 A1* | 3/2011 | Pederson | .............. | F16K 11/074 |
| | | | | 137/625.15 |
| 2013/0174927 A1* | 7/2013 | Wan | ....................... | F16K 11/02 |
| | | | | 137/625.15 |

* cited by examiner

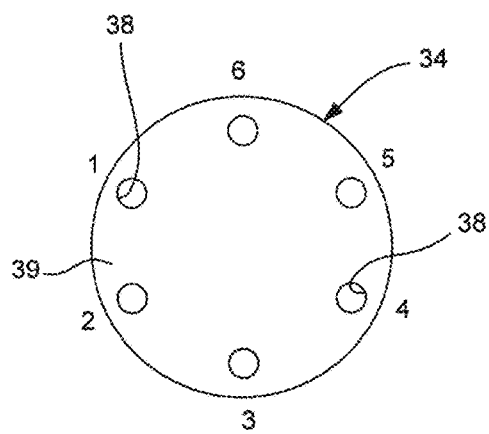
*(Prior Art)*
FIGURE_2
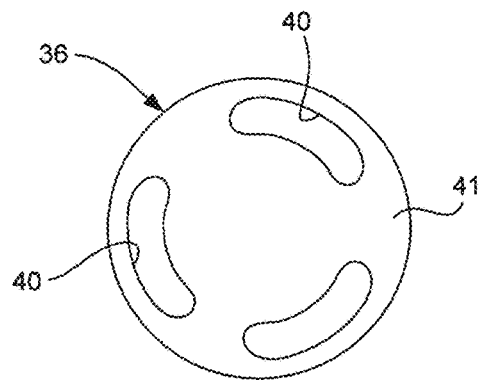
*(Prior Art)*
FIGURE_3
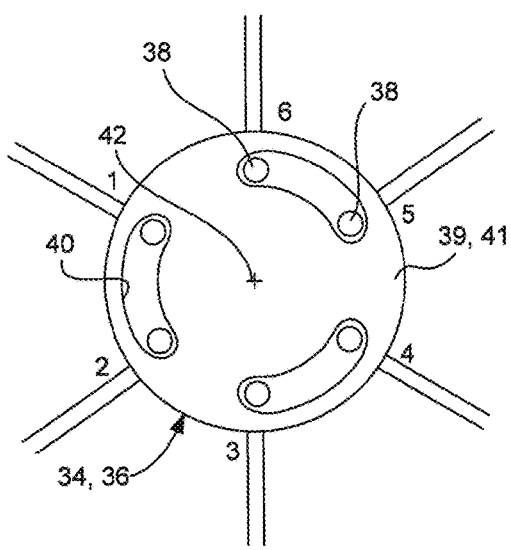
*(Prior Art)*
FIGURE_4A
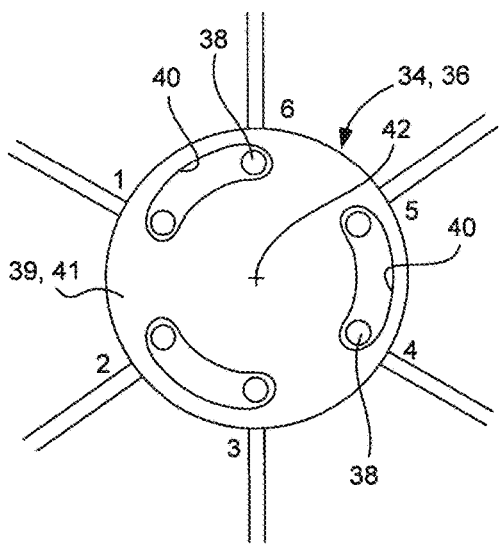
*(Prior Art)*
FIGURE_4B

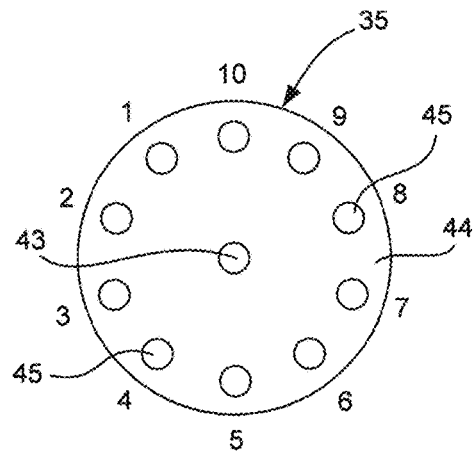
*(Prior Art)*
*FIGURE_5*
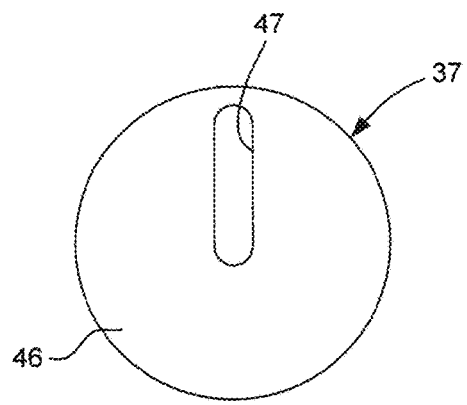
*(Prior Art)*
*FIGURE_6*
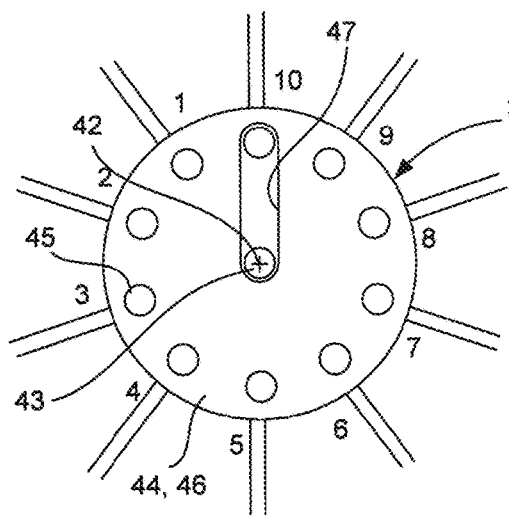
*(Prior Art)*
*FIGURE_7*
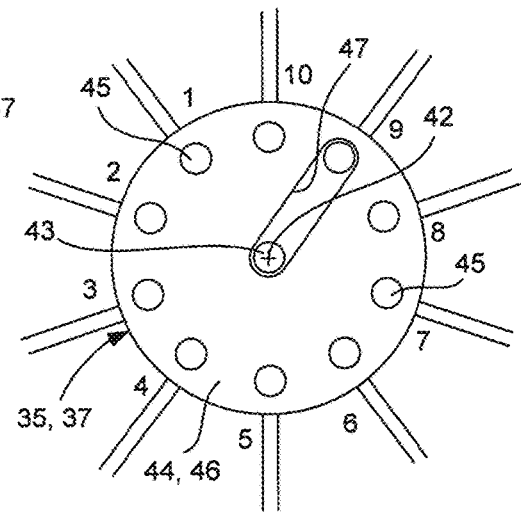
*(Prior Art)*
*FIGURE_8*

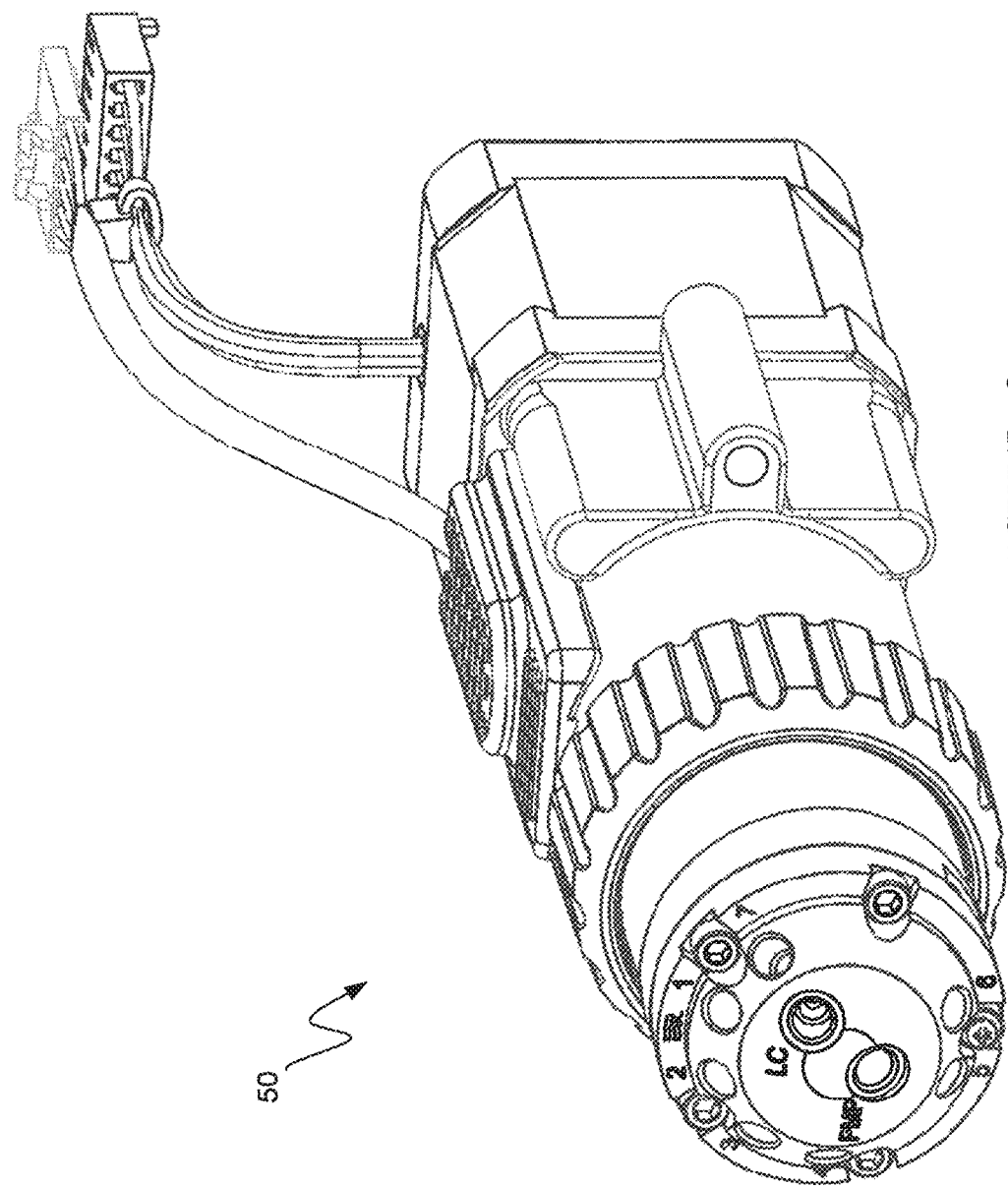
FIGURE_9

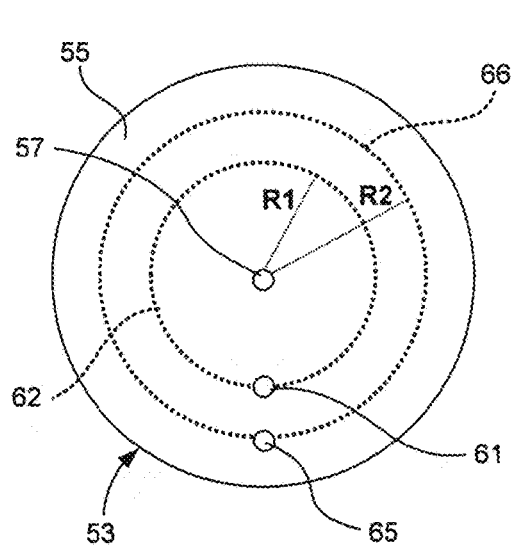
FIGURE_10
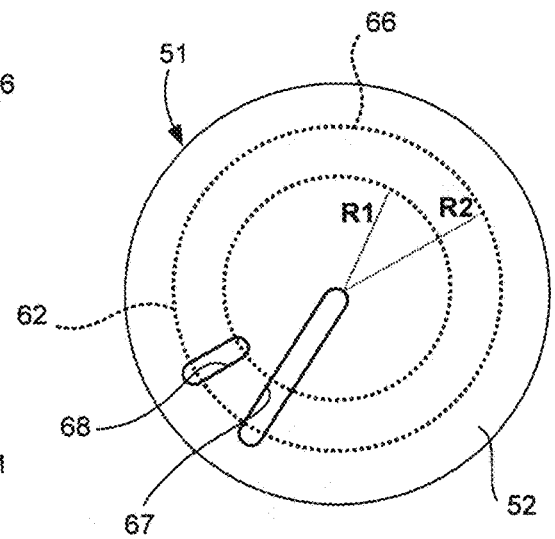
FIGURE_11
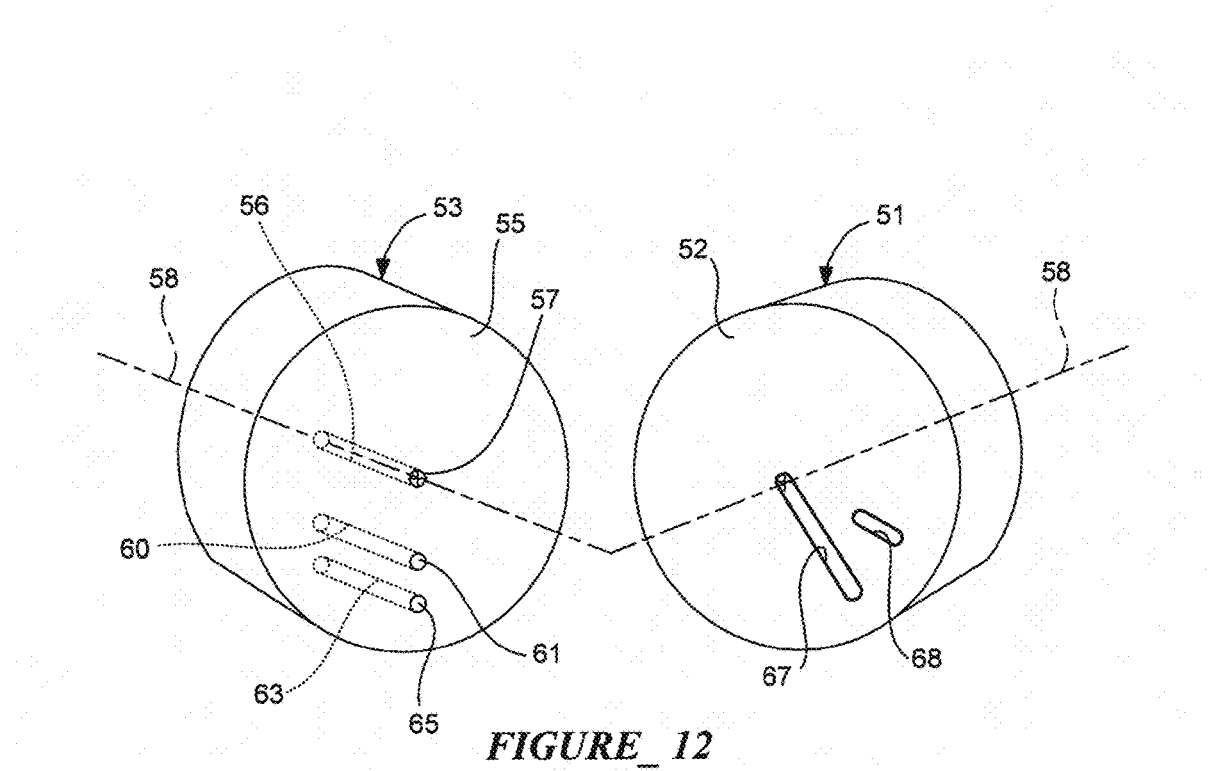
FIGURE_12

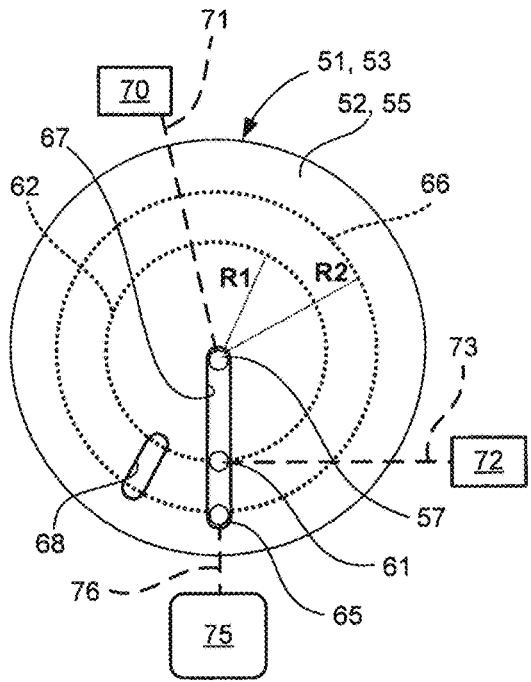
FIGURE_13
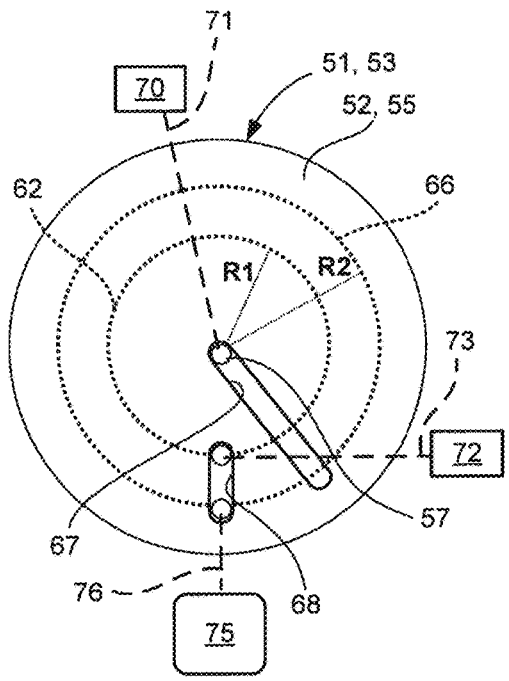
FIGURE_14
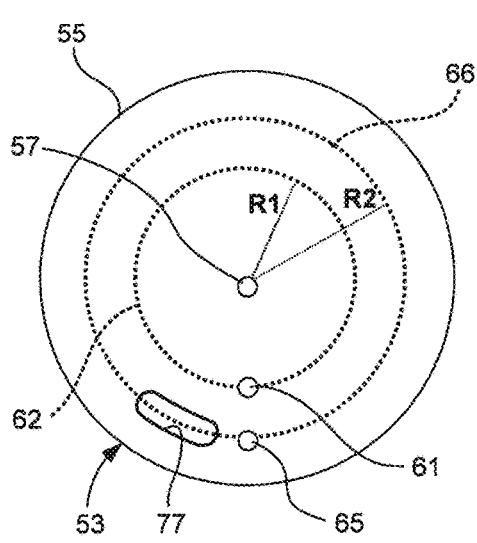
FIGURE_15
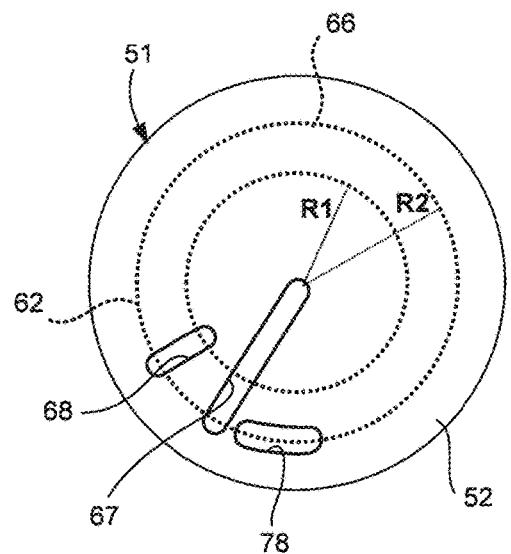
FIGURE_16

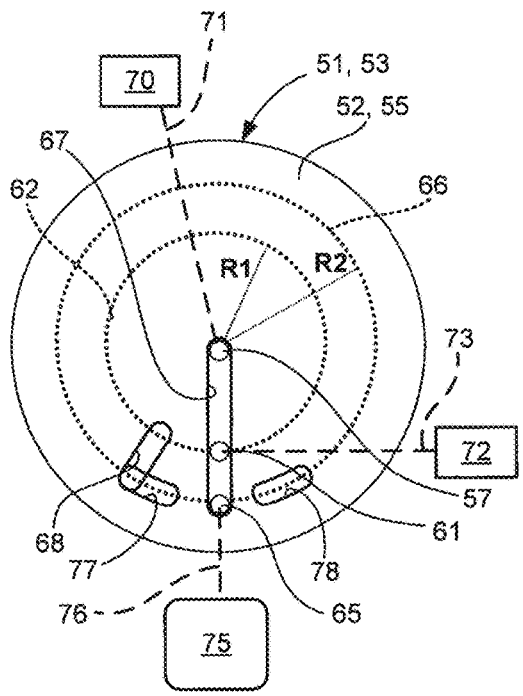
FIGURE_17
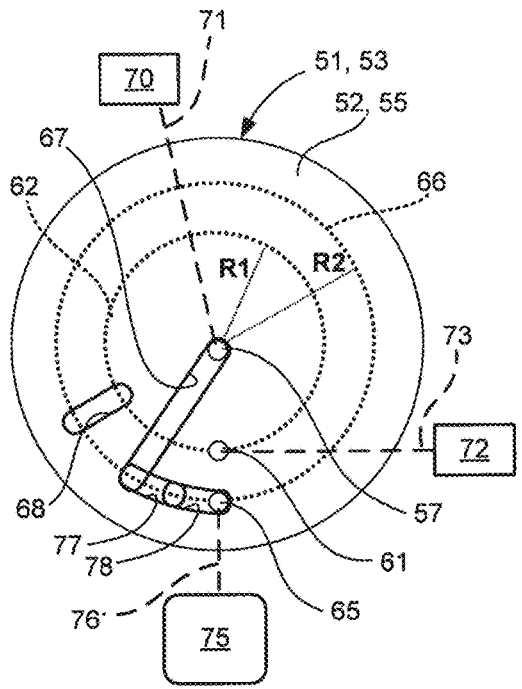
FIGURE_18
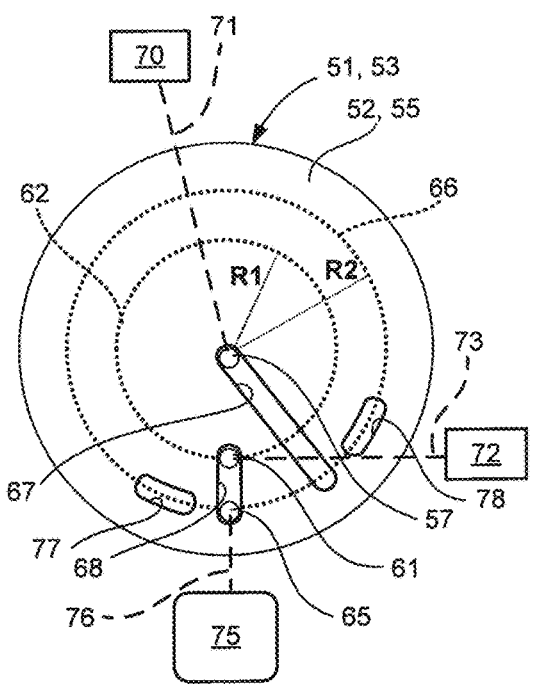
FIGURE_19

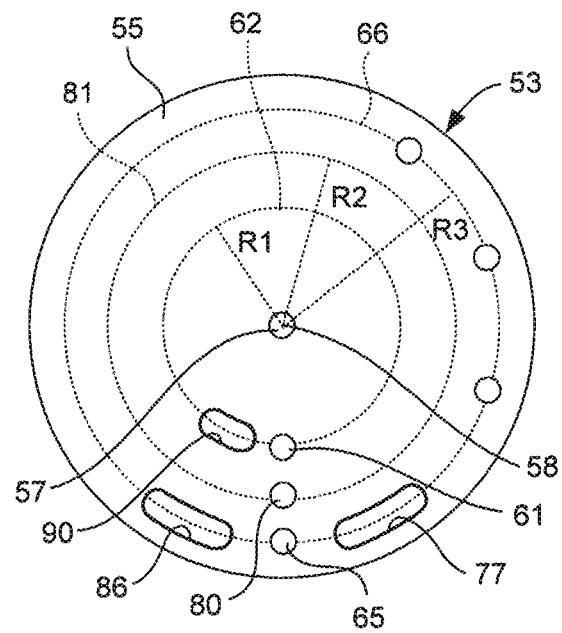
*FIGURE_20*
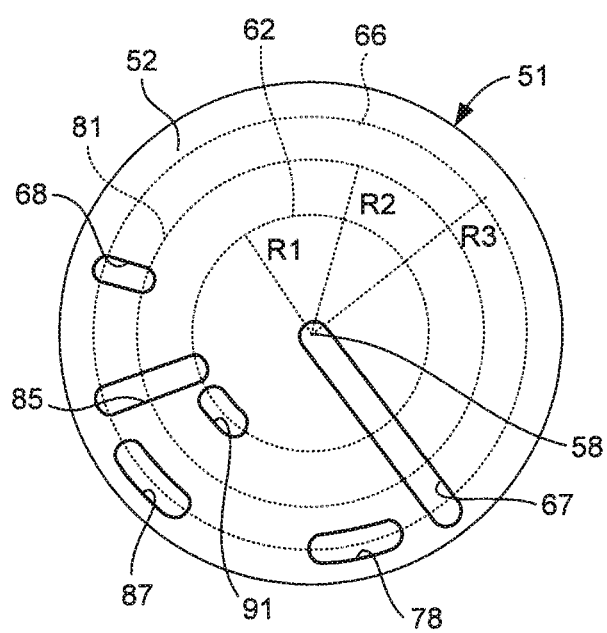
*FIGURE_21*

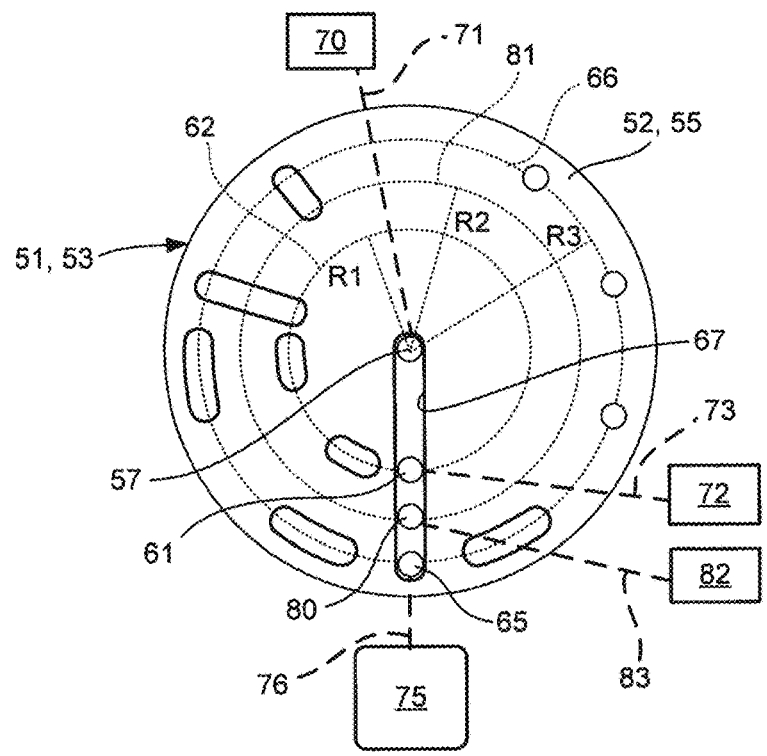
*FIGURE_22*
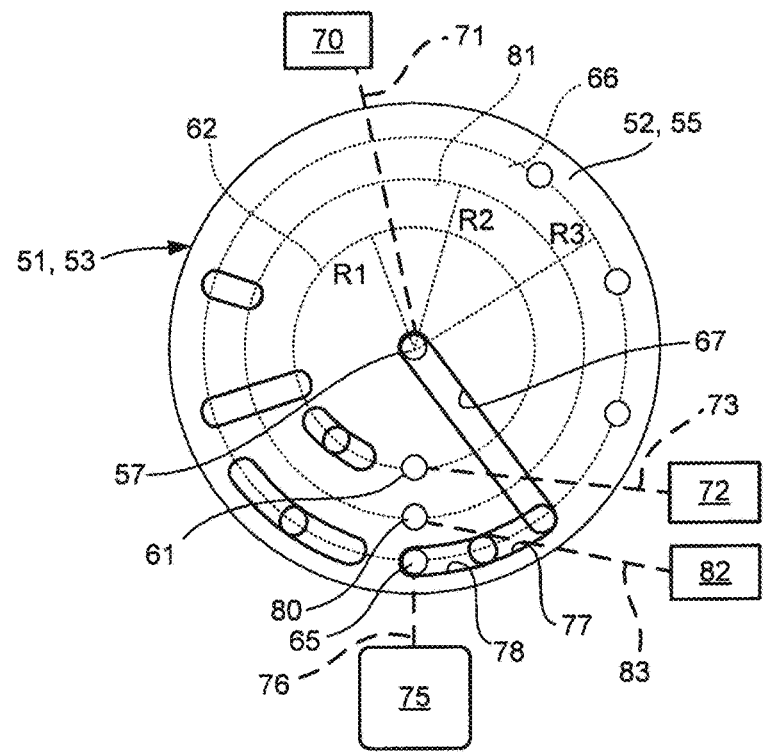
*FIGURE_23*

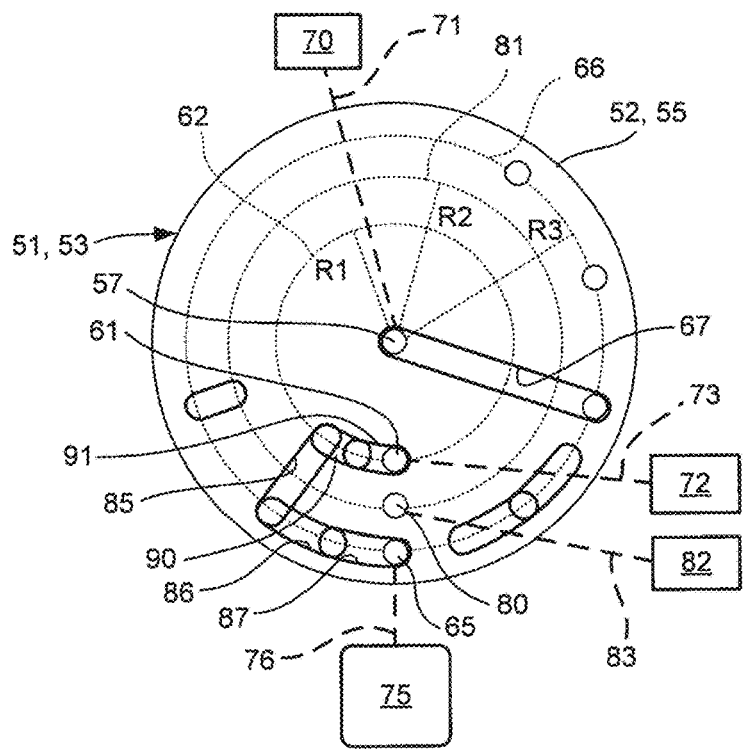
*FIGURE_24*
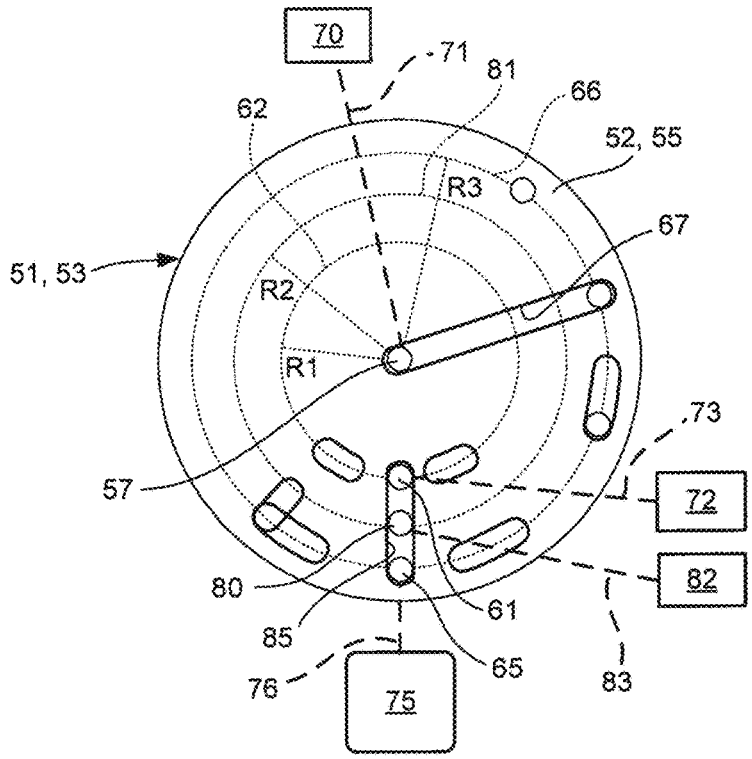
*FIGURE_25*

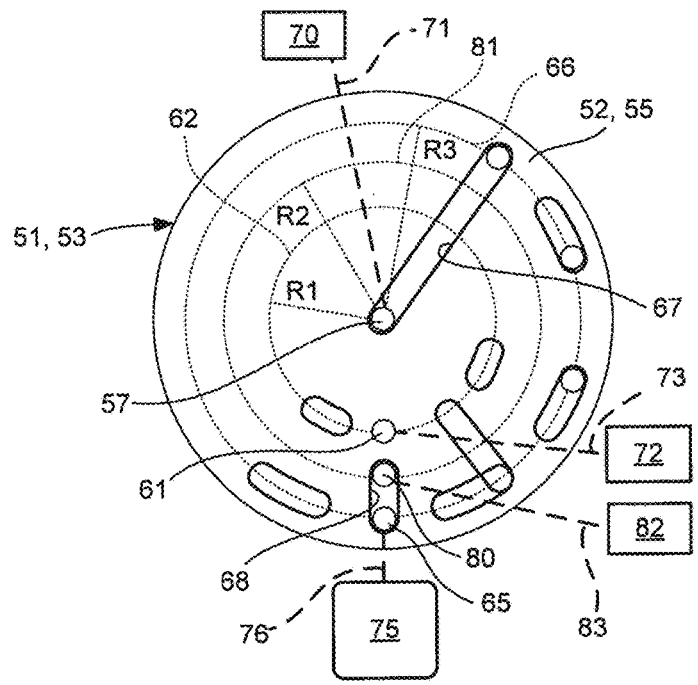
*FIGURE_26*
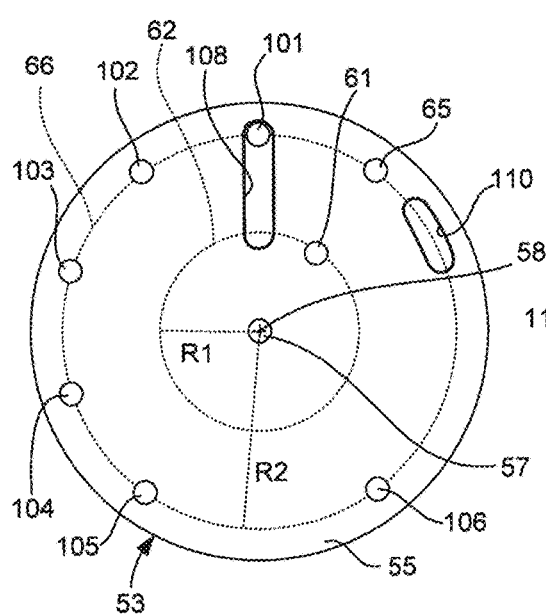
*FIGURE_27*
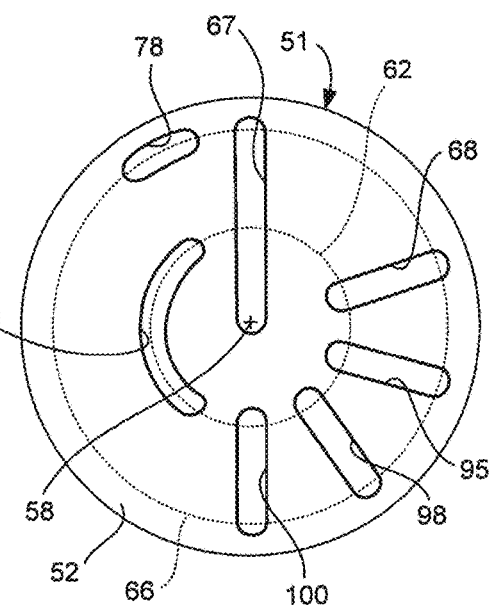
*FIGURE_28*

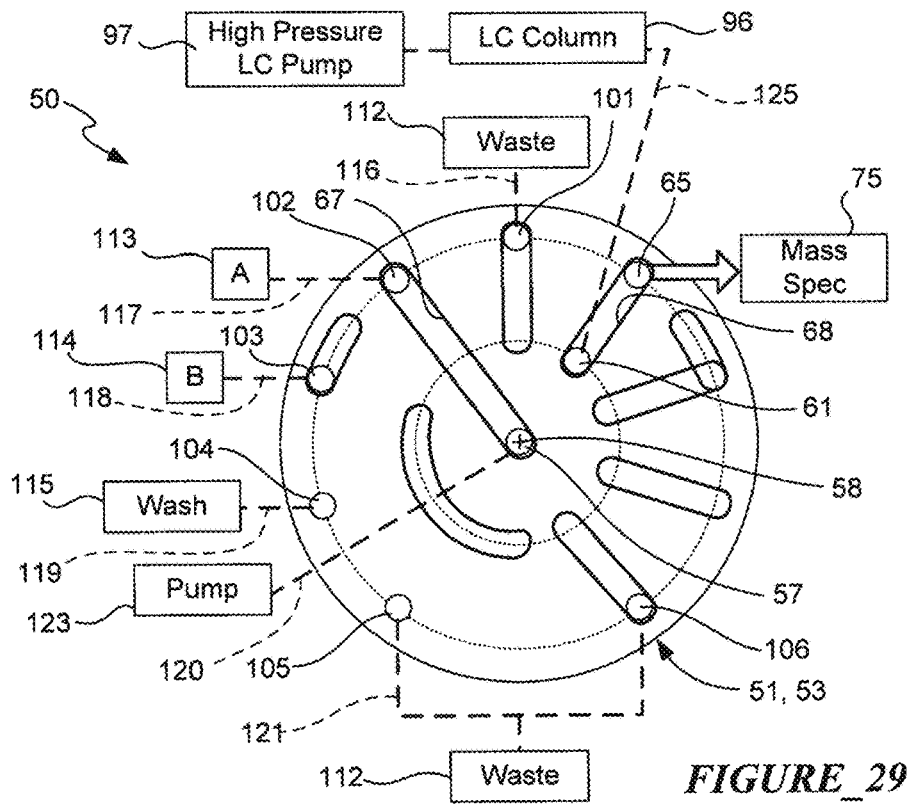
*FIGURE_29*
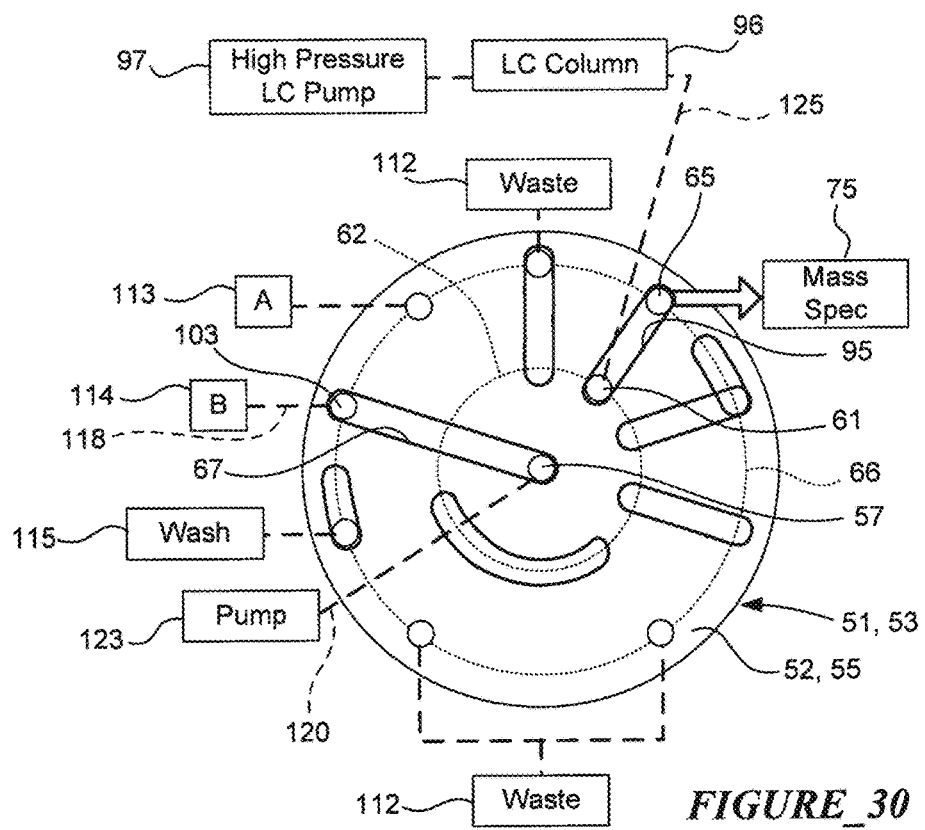
*FIGURE_30*

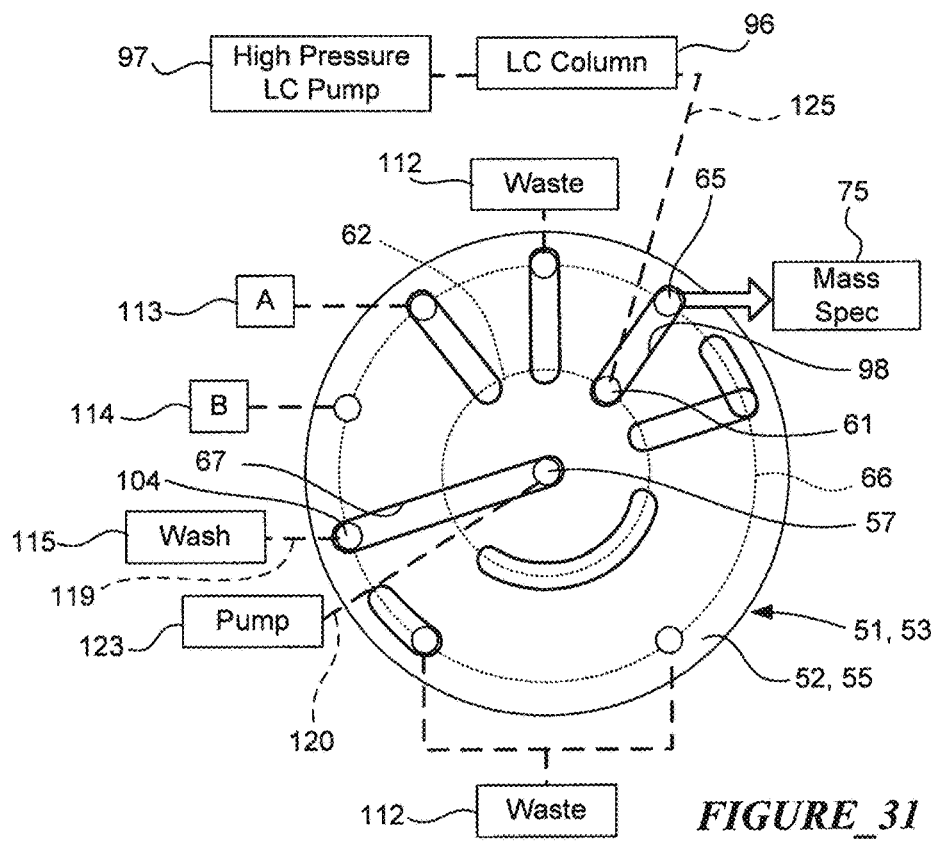
*FIGURE_31*
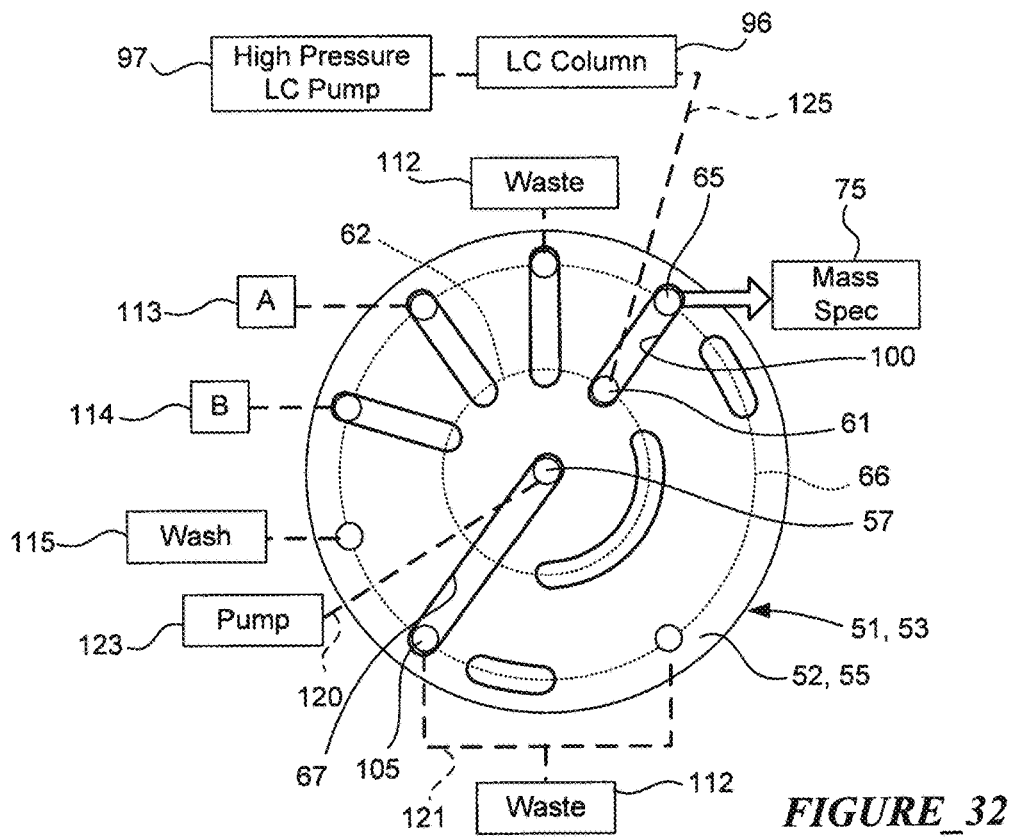
*FIGURE_32*

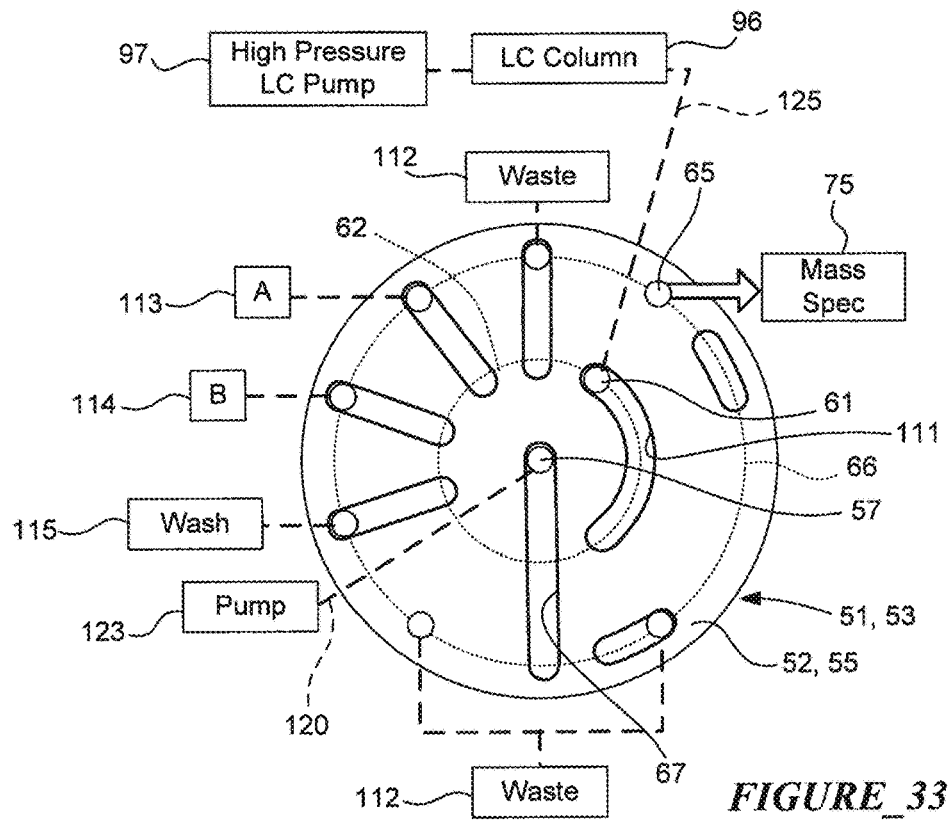
*FIGURE_33*
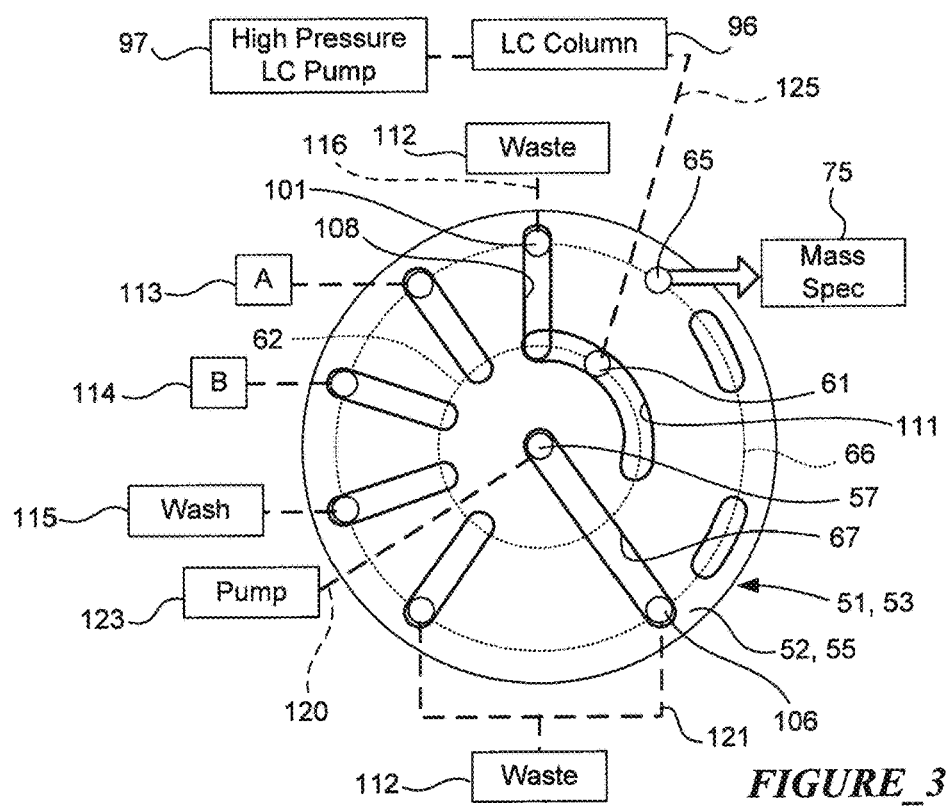
*FIGURE_34*

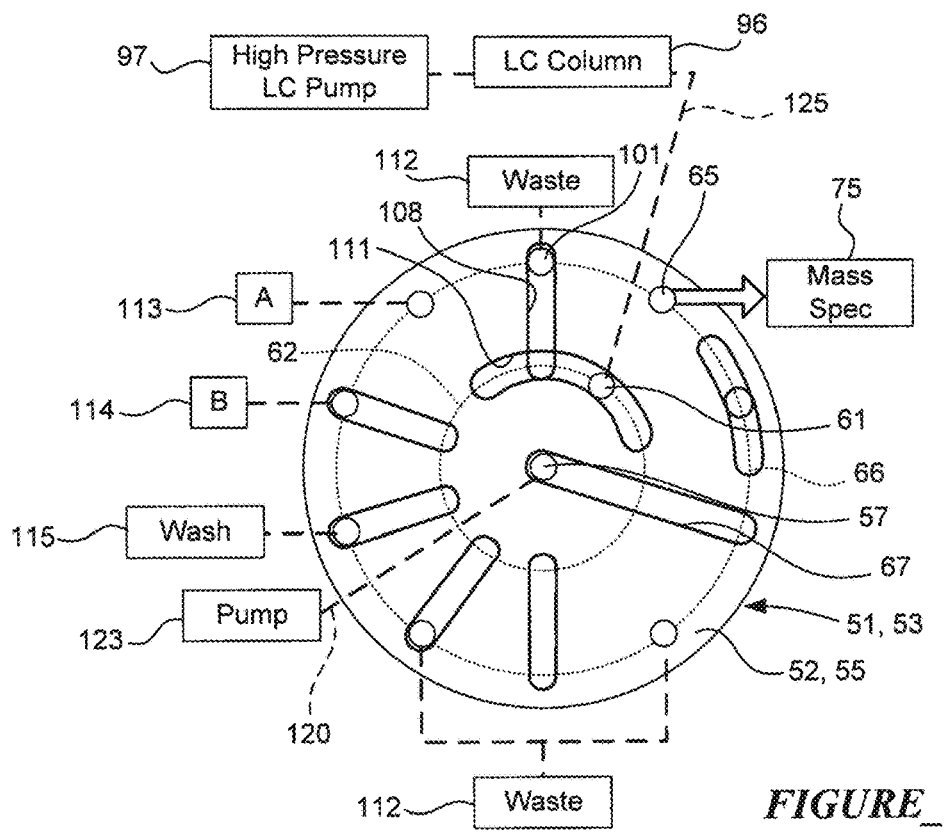
*FIGURE_35*
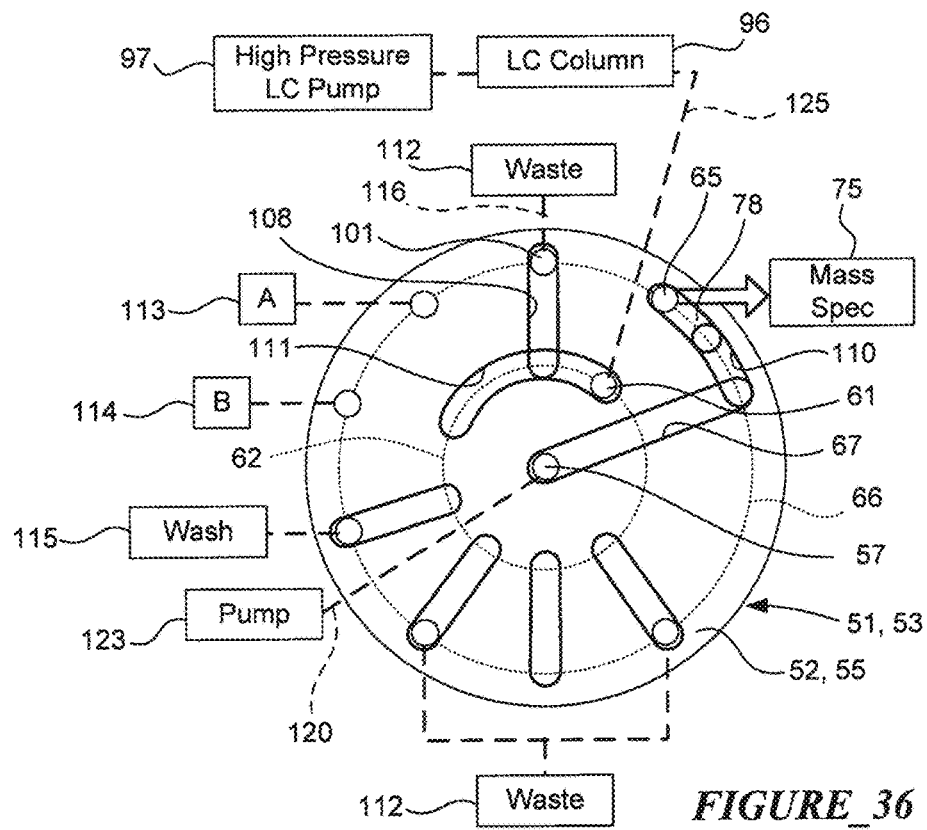
*FIGURE_36*

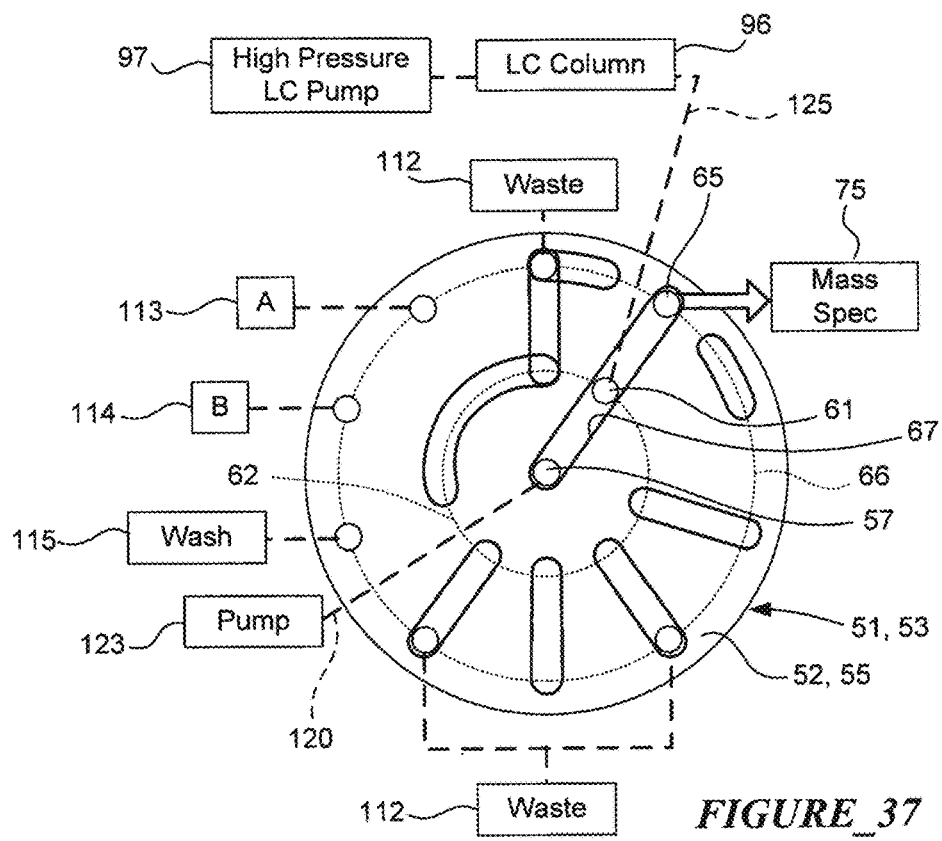
*FIGURE_37*
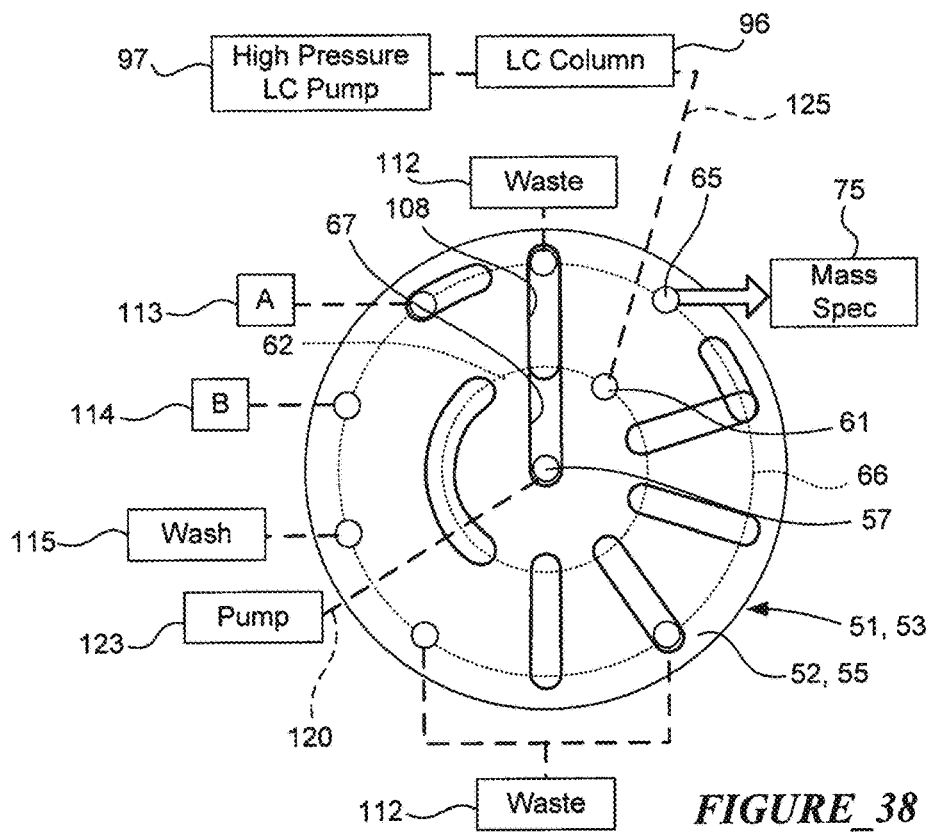
*FIGURE_38*

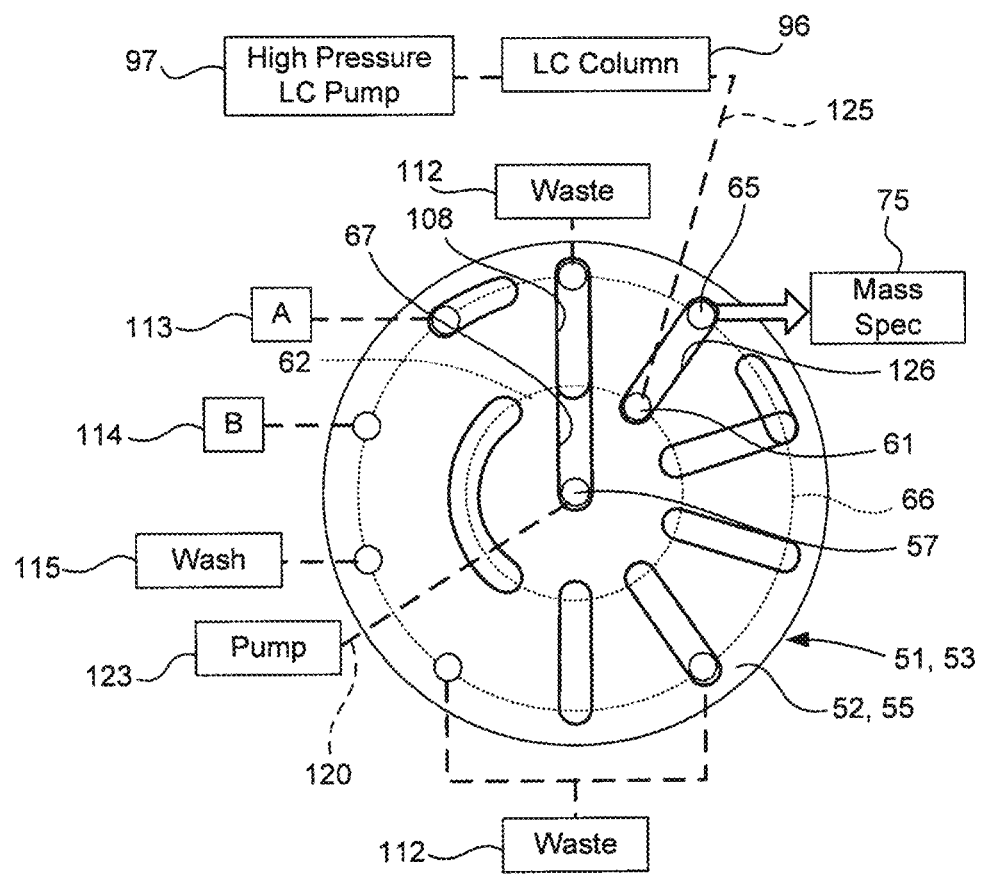
FIGURE_39

MULTI-POSITION, MICRO-FLUIDIC VALVE ASSEMBLY WITH MULTIPLE RADIAL GROOVES TO ENABLE INDIVIDUAL OR COMBINED FLOWS

RELATED APPLICATIONS

This application claims priority under 35 U.S.C. § 119(e) from U.S. Provisional Patent Application No. 62/081,256, filed Nov. 18, 2014, entitled "SELECTOR VALVE FLOWS WITH MULTIPLE RADIAL GROOVES TO ENABLE INDIVIDUAL OR COMBINED" which is incorporated by reference in its entirety.

FIELD OF THE INVENTION

The present invention relates generally to multi-position, micro-fluidic valve assemblies, and more particularly, relates rotary shear valve assemblies utilized in Liquid Chromatography (LC) and other analytical methods that direct fluid along alternate paths into a flowstream.

BACKGROUND OF THE INVENTION

Traditional Liquid Chromatography (LC) delivery systems 30 typically utilize two rotary shear valves: a rotary shear diverter valve 31 and rotary shear selector valve 32, as shown in FIG. 1. The diverter valve 31 is switched to send LC flow into an analysis system such as a Mass Spectrometer source (an output device listed as "source" in FIG. 1) or waste, and allows the output from the selector valve 31 to feed into the analysis system. When the selector valve 31 is routing a liquid reagent (e.g., a calibrant) and a wash agent to the analysis system, via the diverter valve 32 (as shown in the position of FIG. 1), the diverter valve sends the LC steam to waste or capture; the two valves are synchronized to ensure minimal interruption of the LC flow. The two valves will be mated with a pump 33 dedicated to aspiration and dispense of the wash and calibrant liquids, and the distance between the components is minimized to reduce dispersion and waste.

Rotary shear valves, such as the rotary shear diverter valve 31 (FIGS. 2-4) and the rotary shear selector valve 31 (FIGS. 5-8) typically employ a stator device 34, 35 with ports and a rotor device 36, 37 with grooves which are compressed together for a fluid-tight seal, at a rotor-stator interface, and rotated relative one another for switching between the ports. For example, as best illustrated in FIGS. 2-4, a rotary shear diverter valve is shown that generally include the disk-shaped stator device 34 (FIG. 2) that includes face holes or ports 38 in a planar stator face 39 thereof the stator device, and the disk shaped rotor device 36 (FIG. 3) with circumferential rotor grooves 40 on a planar rotor face 41.

Simplistically described, the rotor face 41 is compressed against the planar stator face 39, forming the fluid-tight seal. The rotor device 36 is coupled to a drive shaft, which in turn, is coupled to a gear assembly positioned between a motor device and the drive shaft, both of which are not illustrated. Hence, when the drive shaft selectively rotates about its common central rotational axis 42, via the motor device, the rotor face 41 is rotated relative to the fixed stator face 39.

In turn, as shown in FIG. 4A which illustrates a rotor/stator interface where the rotor grooves 40 are superimposed over the ports 38 of the stator face, the grooves 40 connect different ports to one another, depending on the position of the valve. In a basic switching valve, selection may be limited to only two alternate paths that connect several inputs to a first or second output, depending on the valve state (FIGS. 4A and 4B).

FIGS. 5-8 show another type of micro-fluidic rotary shear valve (i.e., a selector valve) with the stator device 35 having an additional central port 43 formed in a stator face 44 thereof which is surrounded by a plurality of outer ports 45. With respect to the rotor device 37, a rotor face 46 thereof provides a radially extending groove 47. By rotating the rotor device 37 about the common central rotational axis 48, connection of the central port 43 to any number of radial ports 45 can be alternately made.

While these valves are reliable, efficient, and highly successful, they have limited switching options, restricting their application. Particularly limiting is the fact that in each position these valves connect ports in a one-to-one mapping. Accordingly, there is a need to provide single valve that has additional functionality, and specifically, there is a need for a valve that can selectively and optionally connect more than one input to a single output at a time.

Moreover, there is a need to enable combining the function of the rotary shear diverter valve and the selector valve into a single component rotor shear valve that reduces sub-system cost, minimizes system fluid path volume and overall component footprint, and allows simultaneous delivery of reagent and LC streams.

SUMMARY OF THE INVENTION

The present invention provides a rotary shear valve assembly including a rotor device having a substantially planar rotor face, and a stator device also having a substantially planar stator face. The stator device defines a first passage extending therethrough that terminates at a central port on the stator face. The central port is coincident with a common central rotational axis of both the rotor face and the stator face. The stator device further defines a second passage extending therethrough that terminates at a second port on the stator face. The second port is radially spaced a radius R1 from the central port. A third passage is included extending through the stator device that terminates at a third port on the stator face, radially spaced a radius R2 from the central port. The third port and the second port are in general linear alignment with the central port and with one another the second port, wherein radius R2 is greater than radius R1. The rotor device includes a first rotor groove defined in the rotor face, and extends radially outward from the common central rotational axis to a position generally at the radius R2 from the central port. The rotor device is rotatably mounted to the stator device for rotation thereof about the rotational axis in a manner enabling fluid-tight, selective relative rotation between the rotor face and the stator face, at a rotor-stator interface, between two or more discrete rotor positions. In accordance with the present invention, when the rotor device is in a discrete first rotor position, the first rotor groove is oriented in radial alignment with, and fluidly connects, the central port and the second port with the third port to one another.

Accordingly, the liquids from two or more fluid input ports can be combined for flow through a single output port. This is advantageous, for example in the field of Liquid Chromatography (LC), in that one or more calibrants can be delivered with a LC stream to support internal calibration of an analysis system such as a Mass Spectrometer. This permits an operator, for instance, to have calibrant ions at the top and bottom of the detection scale on interest, with the analyte anticipated to appear somewhere in the middle of the m/z range bounded by the calibrant m/z ratios.

In one specific embodiment of the present invention, the central port and the second port are input ports for input of respective liquids therethrough, and the third port is an output port for output of the respective liquids therethrough.

In another configuration, the central port and the third port are input ports for input of respective liquids therethrough, and the second port is an output port for output of the respective liquids therethrough.

In yet another specific embodiment, the second port and the third port are input ports for input of respective liquids therethrough, and the central port is an output port for output of the respective liquids therethrough.

Still another configuration provides that the rotor device further includes a first rotor channel defined in the rotor face, extending in a direction radially outward from the common central rotation axis. The second rotor commences from a first radial location generally at the radius R1 from the central port and terminates at to a second radial location generally at the radius R2 from the central port. When the rotor device is in a discrete second rotor position, which is rotationally offset about the central rotational axis from the first rotor position, the first rotor channel is oriented in radial alignment with, and fluidly connects, the second port with the third port.

In another specific embodiment, the rotor device further includes a circumferential rotor groove, having a first arc length, that is defined in the rotor face. The circumferential rotor groove extends circumferentially about the central rotational axis, along an imaginary circle having a radius R2. The stator face also includes a circumferential stator groove, having a second arc length, that extends circumferentially around the imaginary circle. When the rotor device is in a discrete third rotor position, rotationally offset about the central rotational axis from the both the first rotor position and the second rotor position, the first rotor groove is oriented in fluid communication with one end of the circumferential stator groove. An opposite end of the circumferential stator groove is oriented in fluid communication with one end of the circumferential rotor groove, while an opposite end of the circumferential rotor groove is oriented in fluid communication with the third port. Accordingly, the central port is in fluid communication with only the third port. The sum of the first arc length of the circumferential rotor groove and the second arc length of the circumferential stator groove is at least as long as the third arc length, at radius R2, as the rotor face rotationally turns moving from the first rotor position to the third rotor position.

In another aspect of the present invention, another rotary shear valve assembly is provided having a rotor device with a substantially planar rotor face, and a stator device also having a substantially planar stator face. The rotor face and the stator face have a common central rotational axis when the rotor device is rotatably mounted to the stator device in a manner enabling fluid-tight, selective relative rotation therebetween, at a rotor-stator interface, between a plurality of discrete rotor positions. The stator device further defines a second passage therethrough that terminates at a second port on the stator face. The second port is contained in a first imaginary circle around the central rotational axis, having a radius R1. The stator device further defines a third passage extending therethrough that terminates at a third port on the stator face. This third port is contained in a second imaginary circle around the central rotational axis, having a radius R2. The third port and the second port are oriented in general linear alignment with the central rotational axis. The rotor device includes a first rotor channel and a second rotor channel each defined in the rotor face, and each extending in a respective direction radially outward from the central rotational axis. Each the first rotor channel and the second rotor channel includes a respective portion thereof contained in the first imaginary circle, and an opposite portion thereof contained in the second imaginary circle. When the rotor device is in a discrete first rotor position, the first rotor channel is oriented in radial alignment with, and fluidly connects, the second port with the third port. Similarly, when the rotor device is in a discrete second rotor position, immediately adjacent the first rotor position and rotationally offset therefrom about the central rotational axis, the second rotor channel is oriented in radial alignment with, and fluidly connects, the second port with the third port. Accordingly, when the rotor device is quickly switched between the first rotor position and the second rotor position, near continuous liquid flow from the second port to the third port can be maintained.

In one specific embodiment, the radius R2 is greater than radius R1, the first imaginary circle is an inner imaginary circle, and the second imaginary circle is an outer imaginary circle.

In another specific embodiment, the second port is an input port for input of respective liquids therethrough, and the third port is an output port for output of the respective liquids therethrough.

In yet another embodiment, the rotor device further includes a third rotor channel defined in the rotor face and extending in a respective direction radially outward from the central rotational axis. The third rotor channel includes an inner portion contained in the inner imaginary circle and an opposite outer portion thereof contained in the outer imaginary circle. Moreover, when the rotor device is in a discrete third rotor position, immediately adjacent the second rotor position and rotationally offset therefrom about the central rotational axis, the third rotor channel is oriented in radial alignment with, and fluidly connects, the second port with the third port. When the rotor device is quickly switched between the second rotor position and the third rotor position, near continuous liquid flow from the second port to the third port can be maintained.

In yet another configuration, the stator device defining a first passage extending therethrough that terminates at a central port on the stator face. The central port is positioned coaxial with the common central rotational axis. The rotor device further includes an elongated first rotor groove defined in the rotor face and has one end coincident and in fluid communication with the central port at the central rotational axis. The first rotor groove extends radially outward therefrom and terminates at an opposite end thereof contained in the outer imaginary circle. Thus, when the rotor device is in a discrete fourth rotor position, the first rotor groove is oriented in radial alignment with, and fluidly connects, the central port and the second port with the third port.

In yet another aspect of the present invention, a rotary shear valve assembly is included having a rotor device having a substantially planar rotor face, and a stator device having a substantially planar stator face. The stator device defines a second passage that extend therethrough and terminates at a second port on the stator face. The second port is contained in a first imaginary circle around the central rotational axis having a radius R1. The stator device further defines a fourth passage that extends therethrough and that terminates at a fourth port on the stator face. The fourth port is contained in a second imaginary circle around the central rotational axis having a radius R2. The stator device further includes a radial stator groove extending in general linear alignment with the central rotational axis and the fourth port. A portion of the stator groove is positioned at the first imaginary circle and an opposite portion is positioned at the second imaginary circle, and in continuous fluid communication with the fourth port. The rotor device further includes a first circumferential rotor groove defined in the rotor face and extending in a direction circumferentially about the central rotational axis on the first imaginary circle. The first circumferential rotor groove having an arc length extending at least two consecutive and adjacent discrete rotor positions. When the rotor device is in a discrete first rotor position, the first circumferential rotor groove is oriented in circumferential alignment with, and fluidly connects, the second port with the inner portion of the stator groove, such that the second port is in fluid communication with the fourth port. Moreover, when the rotor device is in a discrete second rotor position, immediately adjacent the first rotor position and rotationally offset therefrom about the central rotational axis, the first circumferential rotor groove is continuously oriented in circumferential alignment with, and continuously fluidly connects, the second port with the inner portion of the stator groove. Accordingly, quickly switching the rotor device between the first rotor position and the second rotor position, continuous liquid flow from the second port to the fourth port can be maintained.

In one specific embodiment, the radius R2 is greater than radius R1, the first imaginary circle is an inner imaginary circle, and the second imaginary circle is an outer imaginary circle.

In another specific embodiment, the second port is an input port for input of respective liquids therethrough, and the fourth port is an output port for output of the respective liquids therethrough.

In still another configuration, the first circumferential rotor groove has an arc length extending at least three consecutive and adjacent discrete rotor positions from the discrete first rotor position to a discrete third rotor position. When the rotor device is in the discrete third rotor position, immediately adjacent the second rotor position and rotationally offset therefrom about the central rotational axis, the first circumferential rotor groove is continuously oriented in circumferential alignment with, and continuously fluidly connects, the second port with the inner portion of the stator groove. Hence, when the rotor device is quickly switched between any of the first rotor position, the second rotor position and the third rotor position, continuous liquid flow from the second port to the fourth port can be maintained.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawings, in which:

FIG. 2 is a top plan view of a prior art stator face of a stator device.

FIG. 3 is a bottom plan view of a prior art rotor face of a rotor device.

FIG. 4A is a top plan view of the prior art stator device of FIG. 1 with the rotor face of the rotor device of FIG. 2 superimposed thereon at a rotor-stator interface, in a first rotor position.

FIG. 4B is the rotor-stator interface of FIG. 4A, shown in a second rotor position.

FIG. 5 is a top plan view of another prior art stator face of a stator device.

FIG. 6 is a bottom plan view of another prior art rotor face of a rotor device.

FIG. 7 is a rotor-stator interface top plan view of the prior art stator device of FIG. 4 with the rotor face of the rotor device of FIG. 6 superimposed thereon at a rotor-stator interface, in a first rotor position.

FIG. 8 is the rotor-stator of FIG. 7, shown in a second rotor position.

FIG. 9 is a top perspective view of a micro-fluidic valve system incorporating the rotary shear valve assembly constructed in accordance with the present invention.

FIG. 10 is a top plan view of a stator face of a stator device constructed in accordance with the present invention.

FIG. 11 is a mirror image, bottom plan view of a rotor face of a rotor device constructed in accordance with the present invention.

FIG. 12 is an exploded top perspective view of a rotor face of the rotor device and a stator face of the stator device, constructed in accordance with the present invention.

FIG. 13 is a schematic representation of a top plan view of the stator device of FIG. 10 with the rotor face of the rotor device of FIG. 11 superimposed thereon at a rotor-stator interface, in a discrete first rotor position.

FIG. 14 is a schematic representation of the rotor-stator interface of FIG. 13, shown in a discrete second rotor position.

FIG. 15 is a top plan view of a stator face of an alternative embodiment stator device constructed in accordance with the present invention.

FIG. 16 is a mirror image, bottom plan view of a rotor face of an alternative rotor device constructed in accordance with the present invention.

FIG. 17 is a schematic representation of a top plan view of the stator device of FIG. 15 with the rotor face of the rotor device of FIG. 16 superimposed thereon at a rotor-stator interface, in a discrete first rotor position.

FIG. 18 is a schematic representation of the rotor-stator interface of FIG. 17, shown in a discrete second rotor position.

FIG. 19 is a schematic representation of the rotor-stator interface of FIG. 17, shown in a discrete third rotor position.

FIG. 20 is a top plan view of a stator face of an alternative embodiment stator device constructed in accordance with the present invention.

FIG. 21 is a mirror image, bottom plan view of a rotor face of an alternative rotor device constructed in accordance with the present invention.

FIG. 22 is a schematic representation of a top plan view of the stator device of FIG. 20 with the rotor face of the rotor device of FIG. 21 superimposed thereon at a rotor-stator interface, in a discrete first rotor position.

FIG. 23 is a schematic representation of the rotor-stator interface of FIG. 22, shown in a discrete second rotor position.

FIG. 24 is a schematic representation of the rotor-stator interface of FIG. 22, shown in a discrete third rotor position.

FIG. 25 is a schematic representation of the rotor-stator interface of FIG. 22, shown in a discrete fourth rotor position.

FIG. 26 is a schematic representation of the rotor-stator interface of FIG. 22, shown in a discrete fifth rotor position.

FIG. 27 is a top plan view of a stator face of an alternative embodiment stator device constructed in accordance with the present invention.

FIG. 28 is a mirror image, bottom plan view of a rotor face of an alternative rotor device constructed in accordance with the present invention.

FIG. 29 is a schematic representation of a top plan view of the stator device of FIG. 27 with the rotor face of the rotor device of FIG. 28 superimposed thereon at a rotor-stator interface, in a discrete first rotor position.

FIG. 30 is a schematic representation of the rotor-stator interface of FIG. 29, shown in a discrete second rotor position.

FIG. 31 is a schematic representation of the rotor-stator interface of FIG. 29, shown in a discrete third rotor position.

FIG. 32 is a schematic representation of the rotor-stator interface of FIG. 29, shown in a discrete fourth rotor position.

FIG. 33 is a schematic representation of the rotor-stator interface of FIG. 29, shown in a discrete fifth rotor position.

FIG. 34 is a schematic representation of the rotor-stator interface of FIG. 29, shown in a discrete sixth rotor position.

FIG. 35 is a schematic representation of the rotor-stator interface of FIG. 29, shown in a discrete seventh rotor position.

FIG. 36 is a schematic representation of the rotor-stator interface of FIG. 29, shown in a discrete eighth rotor position.

FIG. 37 is a schematic representation of the rotor-stator interface of FIG. 29, shown in a discrete ninth rotor position.

FIG. 38 is a schematic representation of the rotor-stator interface of FIG. 29, shown in a discrete tenth rotor position.

FIG. 39 is a schematic representation of an alternative embodiment rotor-stator interface of FIG. 29, shown in a discrete tenth rotor position.

DETAILED DESCRIPTION OF THE INVENTION

Figure 1:
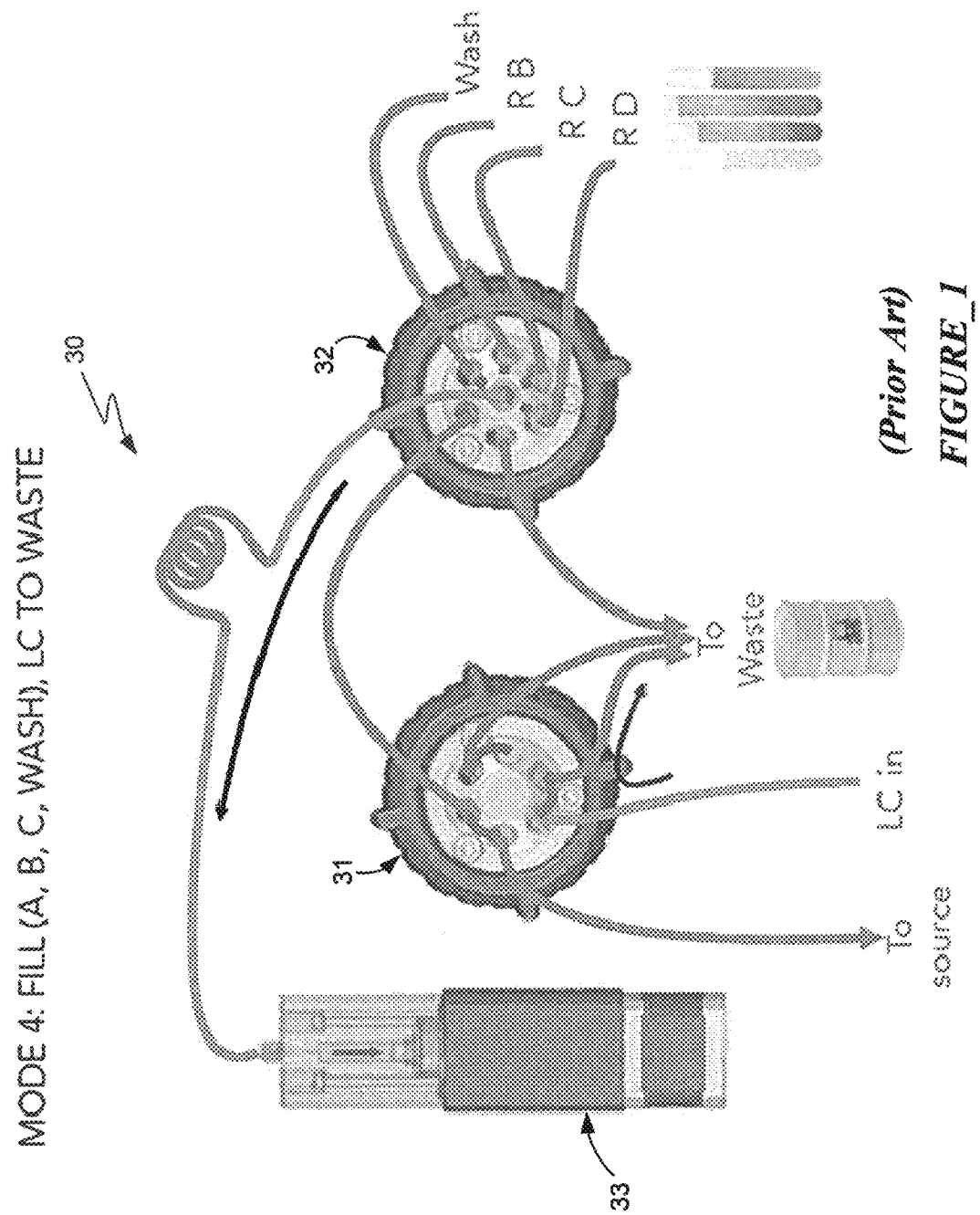
FIG. 1 is a schematic representation of a conventional Liquid Chromatography (LC) delivery system that utilizes a diverter rotary shear valve and a selector rotary shear valve.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like numerals throughout the various figures.

Turning now to FIGS. 9-13, a rotary shear valve assembly 50 is provided having a rotor device 51 (FIG. 11) with a substantially planar rotor face 52, and a stator device 53 (FIG. 10) having a substantially planar stator face 55. The stator device 53 defines a first passage 56 (FIG. 12) extending therethrough that terminates at a central port 57 on the stator face 55. The central port 57 of the stator device 53 is oriented at a common central rotational axis 58 (FIG. 12) of both the rotor face 52 and the stator face 55 when adjacent and operationally contacting one another. The stator device 53 further defines a second passage 60 extending therethrough that terminates at a stator second port 61 on the stator face 55. This second port 61 is radially spaced a radius R1 from the central port 57 (as shown contained in an inner imaginary circle 62 in FIG. 10). The stator device 53 further defines a third passage 63 extending therethrough that terminates at a stator third port 65 on the stator face 55. This third port is radially spaced a radius R2 from the central port (as shown contained in an outer imaginary circle 66 in FIG. 10), and is further in general linear alignment with the central port 57 and the second port 61, wherein the radius R2 is greater than the radius R1.

As best shown in FIGS. 11 and 12, the rotor device 51 further includes a first rotor groove 67 defined in the planar rotor face 52 and extending in a direction radially outward from the common central rotational axis 58 and terminating at a position generally contained in the outer imaginary circle 66, having radius R2 from the central port 57. The rotor device 51 is to be rotatably mounted to the stator device 53 for rotation thereof about the rotational axis 58 in a manner enabling fluid-tight, selective relative rotation between the rotor face 52 and the stator face 55, at a rotor-stator interface, between two or more discrete rotor positions.

Briefly, the terms "contained in" references the fact that the position of the port or position of the portion of the groove or channel is such that sufficient fluid communication is provided therebetween to permit liquid flow. Hence, the groove or channel could extend beyond the port to be aligned therewith.

In accordance with the present invention, when the rotor device 51 is in a discrete first rotor position of the two or more discrete rotor positions, as illustrated in FIG. 13, the first rotor groove 67 is oriented in radial alignment with, and fluidly connects, the central port 57, the second port 61 and the third port 65. That is, in terms of liquid flow, two ports could utilized as input ports to combine two different liquids, such as an LC stream and a calibrant, while the remaining port functions an outlet to a Mass Spectrometer, for example.

Preferably, the central port 57 and the second port 61 are inlet ports, while the third port 65 is an outlet port. It will be appreciated, however, that the outlet port could be positioned at the second port 61, while the central port 57 and the third port 65 function as the inlet ports, or the central port could function as the outlet port, while the two remaining outer ports function as the inlet ports. Moreover, there could be instances were two of the ports function as outlet ports while the remaining port functions as an inlet port. For the ease of description, however, only one output port will be observed which is located on the outermost radii, which in this example is along the outer imaginary circle 66, having at radius R2. The remaining ports will be input ports unless otherwise specified.

This specific embodiment of providing two or more stator input ports (as will be described below) and one stator output port is particularly advantageous in the field of Liquid Chromatography (LC), as mentioned, in that one or more calibrants can be delivered with a LC stream to support internal calibration of an analysis system such as a Mass Spectrometer. This permits an operator, for instance, to have calibrant ions at the top and bottom of the detection scale on interest, with the analyte anticipated to appear somewhere in the middle of the m/z range bounded by the calibrant m/z ratios.

Referring back to FIGS. 12-14, an exemplary embodiment of the stator device 53 and the rotor device 51 is illustrated that constitute the dynamic elements of the valve assembly 50 that is the subject of the present invention. The stator device 53, as mentioned, includes the central port 57 (an input port) coincident with the central rotational axis 58 of the valve assembly 50, while the second port 61 and the stator third port 65 are located on at least two concentric rings at radial distances "R1" and "R2" from the central port. As indicated above, the stator second port 61 is an input port while the stator third port 65 is an outlet port. The number of radii may be larger than two; a third and even a fourth concentric ring of stator ports may be located at radial distances "R3" (FIGS. 20-26) and "R4," from the central port 57.

Moreover, while only a single stator port 61 is shown located a radial distance "R1" from the central port 57, it will be appreciated that more than one port may be contained in the inner imaginary circle 62. Similarly, more than one stator port may be contained in the outer imaginary circle 66.

The rotary shear valve assembly 50 that is the subject of this invention, as mentioned, also includes a rotor device 51, an exemplary embodiment of which is shown in FIG. 11. The rotor face 52 of the rotor device 51 includes an elongated first rotor groove 67 that extends radially away from the central port 57 to at-least-one stator port (e.g. the third port 65) oriented along the outer imaginary circle 66 which has a radius, R2, from the central port 57. In this specific embodiment, the rotor face 52 also include a shorter first rotor channel 68, extending in a direction radially outward from the common central rotation axis 58. This first rotor channel is rotationally off-set from the first rotor groove 67 along the rotation axis 58, both of which are aligned with a respective discrete rotor position, as will be described. One portion or end of the first rotor channel 68, closest to the central port, is contained in the inner imaginary circle 62, having radius R1, while the opposite portion or end thereof is contained in the outer imaginary circle 66, having radius R2.

It will be appreciated that the orientation of the rotor face 52, as shown in FIG. 11, is actually the inverse or mirror image thereof (as correctly shown in FIG. 12). Such inverse orientation of the rotor face 52 is shown for the ease of description, and to illustrate the relationship between the rotor face 52 and the stator face 55 when the rotor device 51 and the stator device 53 are mounted together at the rotor-stator interface. Moreover, such inverse or mirror image orientations are also applied to the embodiments of FIGS. 16, 21 and 28.

During operation of the valve assembly 50, the rotor device 51 and stator device 53 are positioned so that the rotor face 52 containing the grooves 67, 68 forms a dynamic seal with the stator face 55, at a rotor-stator interface, and the rotor grooves align with different stator ports as the valve switches from one discrete position to another. Described simplistically, applying axial compressive pressure, depending upon the application, enables a wide range of pressure applications (e.g., from low pressure to very high pressure micro-fluidic liquid flow).

Referring now to FIGS. 13 and 14, a schematic representation of two discrete rotational positions of this embodiment of the valve are illustrated and described. In the discrete first rotor position (FIG. 13), the elongated first rotor groove 67 of the rotor device 51 is oriented in linear alignment with, and fluidly coupling, the central port 57, the second port 61 and the third port 65. In accordance with this aspect of the present invention, liquid can be conveyed from a first fluid reservoir 70 (which for example could be a pump device) to central port 57, via external tubing 71, and liquid from the second fluid reservoir 72 to the second port 61, via external tubing 73, to the output third port 65, when fluid communication is provided be the aligned first rotor groove. From there, the combined liquid flow may routed to the output device 75, via external tubing 76. Depending upon the application, the output device 75 might be a flow cell, chromatographic column, or other fluidic device, for example.

In the discrete second rotor position, as best shown in FIG. 14, the rotor face is rotated counterclockwise from the discrete first rotor position of FIG. 13. The shorter first rotor channel 68 of the rotor device 51 is positioned into alignment with the stator second port 61 and the third port 65, fluidly coupling them with one another. Hence, only the liquid from the second fluid reservoir 72 can be conveyed to the output device 75, via the second port 61, first rotor channel 68 and third port 65.

Accordingly, through the first and discrete second rotor positions of the valve assembly, liquid from second fluid reservoir 72 may be routed independently to output device 75, or combined with the output of first fluid reservoir 70, and directed through the same port, and from thence to the output device 75.

In accordance with another aspect of the present invention, turning now to FIGS. 15-19, an alternative embodiment of this valve assembly is provided, further including a short circumferential stator groove 77 formed in the stator face 55 of the stator device, and a short outer circumferential rotor groove 78 formed in the rotor face 52 of the rotor device 51. These short arc segments, in this configuration, and as shown in the discrete third rotor position of FIG. 18, are oriented in the outer imaginary circle 66 of radius R2 and configured to fluidly communicate with one another. Accordingly, in the third rotor position, the arc lengths are sufficiently long, relative one another, to overlap at the respective ends thereof.

Referring now to the stator face 55 of FIG. 15 and an the mirror image of the rotor face 52 of FIG. 16, the relative orientations therebetween correspond to the discrete third rotor position of FIG. 18. In FIG. 15, for instance, the arc segment of the circumferential stator groove 77 is oriented to extend along the outer imaginary circle 66, and positioned clockwise from the stator third port 65.

In a similar manner, as illustrated in FIG. 16, the arc segment of the circumferential rotor groove 78 is oriented to extend along the outer imaginary circle 66, although positioned counterclockwise from the outermost radial end of the first rotor groove 67. As mentioned, the rotor face 52 of the rotor device is actually inverted to illustrate the relationship when the opposing rotor face and stator face are mounted together during operation.

When the rotor face 52 is oriented in the discrete first rotor position of FIG. 17 (which corresponds to that of the embodiment shown in FIG. 13) and is rotated clockwise about rotational axis 58 one discrete rotor position (i.e., from the first rotor position to the third rotor position shown in FIG. 18), the outermost radial end of the first rotor groove 67 is positioned into fluid communication with one end of the fixed circumferential stator groove 77. Simultaneously, the clockwise rotating circumferential rotor groove 78 is oriented such that one end of the circumferential rotor groove is positioned to overlap with an opposite end of the circumferential stator groove 77 for fluid communication therebetween, while the other opposite end thereof is positioned for fluid communication with the third port 65.

In this configuration, a complete continuous fluid path is generated from central port 57, through radial first rotor groove 67, circumferential stator groove 77, circumferential rotor groove 78, and out through the third port 65. Accordingly, liquid from the first fluid reservoir 70, via external tubing 71, can be completed independently directed to the output device 75, via external tubing 76.

It will be appreciated that the arc length of each circumferential stator groove 77 and rotor groove 78 must collectively span at a little more than the arc length of the arc segment spanning the distance at the outer imaginary circle 66 from the discrete first rotor position (FIG. 17) to the third rotor position (FIG. 18). Such cooperation assures sufficient fluid communication for the overlapping ends of the circumferential grooves (as viewed in FIG. 18). While the arc lengths of these circumferential grooves are preferably generally equal to one another, this need not be the case. That is, as long as the sum of the arc lengths of the circumferential grooves collectively span the aforementioned arc length, liquid communication therebetween will be enabled.

As is also shown in FIGS. 17 and 19, in this embodiment, the discrete first rotor position of FIG. 17 corresponds to that of FIG. 13, while the discrete second rotor position of FIG. 19 correspond to the second rotor position of the previous embodiment of FIG. 14. That is to say, in the first rotor position (FIG. 17), fluid is conveyed from the central port 57 and the second port 61 to the third port 65 by the long radial first rotor groove 67, while in the discrete second rotor position (FIG. 19) fluid is conveyed only from input of the second port 61 to the output of the third port 65, via the short radial first rotor channel 68. In both positions, via external tubing, liquid flow to the output device 75 can be generated.

Thus, it can be seen that using three adjacent discrete rotor positions of the shear valve assembly, fluid from the first fluid reservoir 70 or from the second fluid reservoir 72 may each independently be directed to output of the third port 65. Also, the two fluids from the respective liquid reservoirs may be combined and directed for output through the third port 65 together. From there, the combined liquids are sent to the output device 75, via external tubing 76. Of note in the diagrams above, in each position, the flow-path is cleanly swept; no dead-ends are present that might lead to contamination, carry-over, or bubble-trapping as the valve switches from one position to another.

Referring now to FIGS. 20-26, a third embodiment of the present invention extends the valve architecture to include a stator third input port 80, located along a middle concentric imaginary circle 81, having a radius R2 of the stator device 53. Briefly, as best shown in FIGS. 20 and 22, this embodiment similarly includes a central input port 57, a stator second input port 61, the stator third input port 80 and a stator output port 65. The central input port 57 is fluidly coupled to the first fluid reservoir 70, via external tubing 71. The second input port 61 is oriented along the inner imaginary circle 62, having a radius R1, and is fluidly coupled to a second fluid reservoir 72, via external tubing 73. Similarly, the third input port 80, oriented along the middle imaginary circle 81, is fluidly coupled to a third fluid reservoir 82, via external tubing 83. Finally, the stator output port 65 is oriented along the outer imaginary circle 66, having a radius R3, and is fluidly coupled to the output device 75, via external tubing 76.

Applying the same concepts mentioned above in the embodiments of FIGS. 10-19, all input port combinations of fluid flow can be controlled for fluid output through the stator output port 65. Similar to the previous embodiments, as best shown in the stator device 53 of FIG. 20, the central port 57, the second input port 61, the third input port 80 and the stator output port 65 are all in a linear alignment, extending through the central rotational axis 58. Also similar, as shown in the rotor device 51 of FIG. 21, the rotor face 52 defines is a radial first rotor groove 67 extending radially from the central rotational axis out to the outer imaginary circle 66, the distance of which is essentially the radius R3.

The rotor face 52 also includes a radial first rotor channel 68 extending radially from the middle imaginary circle 81 to the outer imaginary circle 66. A third rotor groove 85 extends radially from the inner imaginary circle 62 to the outer imaginary circle 66. Finally, viewing both FIGS. 20 and 21, the addition of outer and inner circumferential stator and rotor groove pairs 86 & 87, and 90 & 91, respectively, all five input fluid flow combinations can be achieved, as will be described. These sets or pair of grooves are in addition to the original pair of outer circumferential stator and rotor grooves 77 and 78 as described in the previous embodiment.

As above indicated, fluid originating from the first fluid reservoir 70, and conveyed by external tubing 71, is routed to central input port 57, while fluid originating from the second fluid reservoir 72, and conveyed by external tubing 73, is routed to stator second input port 61. Finally, fluid contained in the third fluid reservoir 82, and conveyed by external tubing 83, is routed to the stator third input port 80.

Referring now to FIG. 22, a discrete first rotor position of this embodiment is illustrated wherein the elongated first rotor groove 67 is linearly aligned with the central input port 57, the second input port 61, the third input port 80 and the stator output port 65. Accordingly, liquids from the first fluid reservoir 70, the second fluid reservoir 72 and the third fluid reservoir 82 can be combined for flow through the first rotor groove 67, and out through the stator output port 65. From there, fluid may be routed, via external tubing 76, to the output device 75.

Rotating the rotor device 51, counterclockwise, one discrete rotor position from the discrete first rotor position (FIG. 22) to the second rotor position (FIG. 23), the elongated first rotor groove 67 aligns with one side of the outer circumferential stator groove 77, along the outer imaginary circle 66. In this position, the outer circumferential rotor groove 78 is placed into fluid communication with the corresponding outer circumferential stator groove 77 thereby generating a complete and continuous fluid path from the central input port 57, through elongated first rotor groove 67, the outer circumferential stator groove 77, the outer circumferential rotor groove 78, and out through stator output port 65. From there the liquid from the first fluid reservoir can be flowed, independently, to the output device 75, via external tubing 76.

As shown in FIG. 23, rotating the rotor device 51, counterclockwise, another discrete rotor position from the discrete second rotor position (FIG. 23) to a discrete third rotor position (FIG. 25), independent liquid flow from the second fluid reservoir 72 to the output device 75 can be achieved. In this discrete third rotor position, the inner circumferential rotor groove 91 aligns with the inner circumferential stator groove 90, on the inner imaginary circle 62 of radius R1, and the outer circumferential rotor groove 87 of the rotor device 51 aligns with outer circumferential stator groove 86 of the stator device, along outer imaginary circle 66 of radius R3. In operation, this provides a complete fluid path from second input port to the stator output port 65. As illustrated, liquid travels in series from the second fluid reservoir 72 to the second input port 61, via external tubing 73, through the inner circumferential rotor groove 91, the inner circumferential stator groove 90, the third rotor groove 85, the outer circumferential stator groove 86, the outer circumferential rotor groove 87, and finally to the stator output port 65.

Rotating the rotor device 51, counterclockwise, yet another discrete rotor position from the discrete third rotor position (FIG. 25) to a discrete fourth rotor position (FIG.

26), the third rotor groove 85 linearly aligns with the second input port 61, the third input port 80 and the stator output port 65. Accordingly, liquid from the second fluid reservoir 72 and the third fluid reservoir 82 can be combined for flow through the third rotor groove 85, and out through the stator output port 65. From there, fluid may be routed, via external tubing 76, to the output device 75.

Finally, rotating the rotor device 51, counterclockwise, still another discrete rotor position from the fourth discrete rotor position (FIG. 26) to a fifth discrete rotor position (FIG. 27), the first rotor channel 68 linearly aligns with only the third input port 80 and the stator output port 65. Accordingly, liquid from only the third fluid reservoir 82 can flow out through the stator output port 65.

Thus, it will be seen that using five adjacent positions of the shear valve assembly 50, liquid fluid from the first, second and third fluid reservoirs 70, 72, and 82 may each independently be directed to the stator output port 65. Additionally, liquids from the second and third fluid reservoirs 72 and 82 may be combined and directed to the stator output port 65 together, while in another discrete rotor position, all three liquids from fluid reservoirs 70, 72, and 82, may be combined and directed to stator output port 65 together. Importantly, in each position, the flow-path is cleanly swept; no dead-ends are present that might lead to contamination, carry-over, or bubble-trapping.

It will be appreciated that in Figures illustrated, there has been no reference to the pumping mechanism by which liquids are conveyed from one place to another. This is due to the fact that the position of the pump(s) is independent of the valve assembly, and is not an essential component of this disclosure. For example, with respect to the embodiment of FIGS. 22-26, a single pump (not shown) might be positioned along the external tubing 76 between stator output port 65 and the output device 75, or even downstream from the output device 75. In such a system, the pump might aspirate liquid from any of the fluid reservoirs 70, 72, and 82 that are alternately connected to the output.

Alternatively, several pumps, placed upstream from the fluid reservoirs 70, 72, and 82, might be used to push fluids from the respective reservoirs to the output device 75. Combinations of such pumping mechanisms can also be envisioned. The choice of how liquids are to be pumped through the valve and, more broadly, through the fluidic system, is one that must be made by consideration of the application and overall fluidic system architecture.

It should also be understood that this invention is not limited to a specific directionality of the valve. While the examples given above refer to stator ports 57, 61, and 80 as inputs, and stator port 65 as an output, the flows might easily be reversed, so that fluid enters through port 65, and exits via one or more of ports 57, 61, and 80, depending upon the valve position. It will further be understood that this invention is not limited to the number and type of rotor grooves, stator grooves, and stator ports that may be included in the valve. The above mentioned embodiments are exemplary only, and additional grooves and ports may provide additional functionality. For example, the fluidic architecture of the valve assembly could be doubled by the inclusion of two additional stator ports located on radii "R2" and "R3", 180 degrees away from the ports already represented at this radii, or the remaining stator ports could be used to provide different functionality.

Turning now to FIGS. 27-38, another aspect of the rotary shear valve assembly is provided. In this configuration, the rotary shear valve assembly 50 includes a rotor device 51 having a substantially planar rotor face 52, and a stator device 53 having a substantially planar stator face 55. The rotor face 52 and the stator face 55 have a common central rotational axis 58 when the rotor device 51 is rotatably mounted to the stator device 53 in a manner enabling fluid-tight, selective relative rotation between the rotor face and the stator face, at a rotor-stator interface, between a plurality of discrete rotor positions (e.g., FIGS. 29-38).

The stator device 53 defines a first passage 56 (same as FIG. 12) extending therethrough that terminates at a central port 57 on the stator face 55. The central port 57 is positioned coaxial with the common central rotational axis 58. The stator device 53 further defines a second passage extending therethrough that terminates at a second port 61 on the stator face 55. The second port 61 is contained in an inner imaginary circle 62 around the central rotational axis 58, having a radius R1. The stator device further defines a third passage 63 extending therethrough that terminates at a third port 65 on the stator face 55, the third port is contained in an outer imaginary circle 66 around the central rotational axis 58, having a radius R2, wherein radius R2 is greater than radius R1. As clearly shown in FIG. 27, and as similar to the previous embodiment above, albeit represented as rotated about the central rotational axis 58, the third port 65 is oriented in general linear alignment with the central rotational axis 58 and the second port 61.

The rotor device 51, as illustrated in FIG. 28 includes a radially extending first rotor channel 68 and a second rotor channel 95, each defined in the rotor face 52. Each radial rotor channel 68, 95 extends in a respective direction radially outward from the central rotational axis 58, and each the first rotor channel 68 and the second rotor channel 95 has a respective inner portion contained in the inner imaginary circle 62 and an opposite outer portion contained in the outer imaginary circle 66.

When the rotor device 51 is in a discrete first rotor position (FIG. 29), the first rotor channel 68 is oriented in radial alignment with, and fluidly connects, the second port 61 with the third port 65. Moreover, when the rotor device 51 is in a discrete second rotor position (FIG. 30), immediately adjacent the first rotor position (FIG. 29) and rotationally offset therefrom about the central rotational axis 58, the second rotor channel 95 is oriented in radial alignment with, and maintains fluid connection with, the second port 61 with the third port 65. In accordance with the present invention, the rotor device 51 quickly switches between the first rotor position and the second rotor position such that near continuous flow stream from the second port 61 to the third port 65 can be maintained.

Accordingly, this is advantageous for Liquid Chromatography systems where it is important to maintain a pseudo-continuous flowstream through the LC column 96, via the High Pressure LC Pump device 97 (FIGS. 29-32). Such a continuous flowstream is imperative since any dead ending of this liquid flow through the LC column 96, via the second port 61, could potentially damage the valve assembly as the High Pressure LC pump 97 continues to operate or interfere with the quality of chromatographic separation through the column. Since the stepped motors employed that rotate the rotor device 51 of the valve assemblies are capable of switching the rotor face between adjacent discrete rotor positions in only about 250 ms, in either direction, the flowstream through the second port 61 and first rotor groove 67 is substantially or nearly continuous, even when the valve is moved to one or more adjacent discrete rotor positions. Moreover, maintaining a continuous, or near continuous, flow stream while switching between various discrete rotor positions, helps maintain the quality of the chromatography.

In accordance with the present invention, thus, when a plurality of radial rotor channels are provided in a sequence of adjacent discrete rotor positions, and each respective rotor channel spans the radial distance between, and contained in, the inner imaginary circle 62 to the outer imaginary circle 66, such substantially near continuous liquid flow stream from the second port 61 to the third port 65 can be maintained when switching therebetween, or any combination thereof.

For example, and as will be described in greater detail below, the rotor face 52 defines a third and forth rotor channel 98, 100 extending radially between, and contained in, the inner imaginary circle 62 and the outer imaginary circle 66. The position of each of the first rotor channel through the fourth rotor channel 100 corresponds, and is in alignment, with a discrete rotor position. Hence rotating the rotor face 52 counterclockwise from the discrete second rotor position (FIG. 30) to the discrete third position (FIG. 31), and similarly, counterclockwise from the discrete third rotor position (FIG. 31) to the discrete fourth position (FIG. 32), enables substantially near continuous liquid flow between the second port 61 to the third port 65. This is advantageous in the primary first rotor groove 67, extending from the central port 57 or the rotational axis 58 out to the outer imaginary circle 66 can perform other functions in during the first four rotor positions while nearly continuously maintaining the flow stream from the LC column to the output device 75 (e.g., the Mass Spectrometer).

Referring back to FIGS. 27 and 28, the groove pattern of the stator face 55 and the rotor face 52 initially patterned off that of the stator device 53 and rotor device 51 of the embodiment of FIGS. 15 and 16, along with additional grooves and ports. Similar to the previous valve embodiments, the stator face 55 defines a central port 57 located on the central rotation axis 58, and additional stator ports 61, contained in the inner imaginary circle 62, and the third stator port 65 and a fourth port 101 through a ninth stator port 106 contained in the outer imaginary circle 66, at radial distances "R1" and "R2" from the central port 57. The outer stator ports circumferentially spaced-apart to align at respective, corresponding discrete rotor positions. Again, similar to the previous valve configurations, the stator second port 61 and the third port 65 are in linear alignment with the central port 57, intersecting the central rotational axis 58.

The stator face 55 of the stator device of this embodiment also defines a radial stator groove 108 and a first circumferential stator groove 110. The radial stator groove 108 is a radially extending groove, having an inner portion contained in inner imaginary circle 62 and an outer portion in communication with the fourth port 101, and contained in the outer imaginary circle 66, having radius "R2." In contrast, the circumferential stator groove 110 extends circumferentially about the outer imaginary circle 66, having an arc length with a distance about one-half the arc length between two consecutive discrete rotor positions, at radius R2. As shown in FIG. 27, the circumferential stator groove 110 is just clockwise of the stator third port 65.

The rotor device 51, as illustrated in FIG. 28, has an elongated first rotor groove 67 that extends radially outward from the central port 57 to a position contained in the outer imaginary circle 66, at outer radius R2. As previously mentioned, the rotor face 52 further defines a plurality of shorter rotor channels (i.e., first rotor channel 66, second rotor channel 95, third rotor channel 98 and fourth rotor channel 100), each of which that extend between, and are contained in, the inner imaginary circle 62 and the outer imaginary circle 66. The rotor device 51 similarly has a shorter arc length outer circumferential rotor groove 78 and a significantly longer arc length inner circumferential rotor groove 111 (the function of which will be described in greater detail below).

The exemplary valve assembly incorporating this embodiment of the present invention illustrated in FIGS. 27 and 28 might be used in a Liquid Chromatography-Mass Spectrometry (LC-MS) application, when connected to the components as described schematically below in reference to FIGS. 29-38.

In this configuration, the LC system include a liquid chromatography (LC) column 96, a Mass Spectrometer 75, a waste receptacle 112, a Reagent bottle A (113), a Reagent bottle B (114), and a wash reservoir 115, which are connected to respective the stator second port 61, third port 65, and the fourth port 101 through the seventh port 104, respectively by external tubing 116-119. Additionally, an aspiration/dispense pump 123 is coupled to the central port 57, via external tubing 120, while the stator eighth port 105 and the ninth port 106 are also coupled to the waste receptacle 112 by external tubing 121.

Briefly, during operation, the high pressure LC pump device 97 continuously pushes sample through LC column 96, via external tubing line 125, to the second port 61, from whence it can be routed to the Mass Spectrometer 75 (FIGS. 29-32) or to the waste receptacle 112 (FIGS. 34-37) depending on the discrete rotor position of the valve. As mentioned, it is imperative not to dead end the liquid flow through the stator second port 61 to avoid damage to the valve assembly or compromising the quality of the chromatographic separation. Simultaneously, the aspiration/dispense pump 123 can aspirate any of Reagent A (113), Reagent B (114), or wash reservoir 115, and dispense them to the waste receptacle 112 or to the Mass Spectrometer 75 either independently, or combined with the output of second port 61. These operations are made clearer in the diagrams below, which show the valve in its various states.

Referring specifically now to FIG. 29, the rotor device 51 is oriented in the discrete first rotor position. As illustrated, the first rotor groove 67 is aligned with the stator second port 61 and the third port 65, enabling the high pressure LC pump device 97 to push sample through LC column 96, via external tubing 125, to the second port 61, and then through the first rotor channel 68 to the stator third port 65. From there, the liquid flow can continue to the Mass Spectrometer 75. Simultaneously, the first rotor groove 67 is in alignment with the stator fifth port 102, wherein the aspiration/dispense pump 123 can aspirate Reagent A, via external tubing 117 and the central port 57, through first rotor groove 67, and on to the aspiration/dispense pump 123, via external tubing 120.

Quickly rotating the rotor device 51 counterclockwise one discrete rotor position from the discrete first rotor position (FIG. 29) to the second rotor position (FIG. 30), the second rotor channel 95 can be quickly aligned with the second port 61 and the third port 65, maintaining nearly continuous free flow therethrough. Accordingly, the High pressure LC pump 97 can perform pseudo-continuously, minimizing effects on the valve assembly and chromatography. Simultaneously, the first rotor groove 67 is in positioned alignment with the stator sixth port 103, enabling the aspiration/dispense pump 123 to aspirate Reagent B, via external tubing 118.

Turning now to FIGS. 31 and 32, the rotor device 51 can be quickly rotated to the discrete third rotor position and the fourth rotor position, respectively. Similarly, in the discrete third rotor position (FIG. 31) the third rotor channel 98 is quickly aligned with the second port 61 and the third port 65, while in the discrete fourth rotor position (FIG. 32) the fourth rotor channel 100 is also quickly aligned with the second port 61 and the third port 65, maintaining nearly continuous free flow therethrough. Again, simultaneously, in the third rotor position (FIG. 31), the first rotor groove 67 is in positioned alignment with the stator seventh port 104, enabling the aspiration/dispense pump 123 to aspirate a wash agent from Wash reservoir 115, while in the fourth rotor position (FIG. 32), the first rotor groove 67 is in positioned alignment with the stator eighth port 105, enabling the aspiration/dispense pump 123 to dispense which ever liquid contained therein to the waste receptacle 112, via external tubing 121.

The discrete fifth rotor position (FIG. 33) is an unused state since the first rotor groove 67 is dead-ended, and would require the aspiration/dispense pump 123 must be turned off. More importantly, the output of LC column 96 through second port 61 is also dead-ended, even though liquid flow enters the inner circumferential rotor groove 111, requiring the High Pressure LC Pump 97 to be turned off.

In the discrete sixth rotor position (FIG. 34) through the ninth rotor position (FIG. 37), another aspect of the present invention will be described, using the stator device 53 and rotor device 51 of same valve configuration of FIGS. 27 and 28. Briefly, it will be appreciated that the discrete rotor positions described heretofore may not coincide exactly with that in the claims for claim clarity. For example, the discrete sixth and seventh rotor positions (FIGS. 34 and 35) described below coincide with the first and second rotor positions of some of the claims.

With that said, the goal is to maintain a continuous flow stream of liquid through the second port 61 which is pushed though the LC column 96 by the high pressure LC pump device 97, and on to the waste receptacle 112. In this configuration, the stator device 53 further defines a radial stator groove 108 extending in general linear alignment with the central rotational axis and the fourth port 101, wherein an inner portion of the radial stator groove 108 is contained in the inner imaginary circle 62 and an opposite outer portion thereof is contained in the outer imaginary circle 66, and in continuous fluid communication with the fourth port 101 (FIG. 27).

With respect to the rotor device 51, as shown in FIG. 28, and as described in general, the rotor face 52 further defines the inner circumferential rotor groove 111 that extends in a direction circumferentially about the central rotational axis 58 on the inner imaginary circle 62. The arc length of the inner circumferential rotor groove 111, at radius R1, extends at least two consecutive and adjacent discrete rotor positions, and in this particular example, from the discrete sixth rotor position (FIG. 34) to the discrete ninth rotor position (FIG. 37).

Accordingly, when the rotor device 51 is in a discrete sixth rotor position (FIG. 34), the inner circumferential rotor groove 111 is oriented in circumferential alignment with, and fluidly connects, the second port 61 with the inner portion of the radial stator groove 108, such that the second port 61 is in fluid communication with the fourth port 101. In this example, the high pressure LC pump device 97 and the LC column 96 are in liquid flow communication with the waste receptacle 112.

When the rotor device 51 is rotated counterclockwise to the discrete seventh rotor position (FIG. 35), immediately adjacent the sixth rotor position and rotationally offset therefrom about the central rotational axis 58, the inner circumferential rotor groove 111 is continuously oriented in circumferential alignment with, and continuously fluidly connects, the second port 61 with the inner portion of the radial stator groove 108. Accordingly, when the rotor device 51 is quickly switched between the sixth rotor position and the seventh rotor position, a continuous liquid flow stream from the second port 61 to the fourth port 101 can be maintained.

In the sixth rotor position of FIG. 34, additionally, the first rotor groove 67 is in positioned alignment with the stator ninth port 106, enabling the aspiration/dispense pump 123 to dispense which ever liquid contained therein to the waste receptacle 112, via external tubing 121. With respect to the seventh rotor position of FIG. 35, the radial first rotor groove 67 is again dead-ended, and the aspiration/dispense pump 123 must be turned off.

Rotating the rotor device 51 counterclockwise the next two discrete positions to the eighth rotor position (FIG. 36) and then onto the ninth rotor position (FIG. 37), the inner circumferential rotor groove 111 is continuously oriented in circumferential alignment with, and continuously fluidly connects, the second port 61 with the inner portion of the radial stator groove 108. Hence quickly switching the rotor device between any one of the sixth rotor position to the ninth rotor position, or combination thereof, continuous liquid flow from the second port 61 to the fourth port 101 can be maintained.

In the discrete eighth rotor position (FIG. 36), the radial first rotor groove 67 is moved into alignment, and thus fluid communication with, the outer circumferential stator groove 110. The outer circumferential rotor groove 78 is similarly rotated to overlap an opposite end of the circumferential stator groove 110, while an opposite end of the rotor groove 78 communicates with the third port 65. Accordingly, whichever liquid has been aspirated into the aspiration/dispense pump line, can now be dispensed directly through the Mass Spectrometer 75.

With respect to the radial first rotor groove 67 in the ninth rotor position of FIG. 37, the elongated radial groove is linearly aligned with the second port 61 and the third port 65. Hence, this is identical to the discrete first rotor positions of the previous embodiments of FIGS. 13 and 17 where the liquids from two input ports 57, 61 can be combined for flow through one output port 65. In this specific embodiment, this position of the valve therefore offers a means by which the liquid output of aspiration/dispense pump 123 and that of the LC column 96 may be combined into a single fluid stream, prior to injection into the Mass Spectrometer 75.

The tenth rotor position (FIG. 38) is another unused state in which the output of the LC column 96 is dead-ended into the rotor face 52, at the second port 61. In this position, the aspiration/dispense pump 123 is routed to waste receptacle 28 via a fluid path comprising external tubing 120, central port 57, radial first rotor groove 67, fourth stator port 101, and external tubing 116.

In summary, it will be seen that this embodiment of the valve assembly can be used to direct the output of an LC column 96 to a Mass Spectrometer 75 or to waste 112, while at the same time enabling an aspiration/dispense pump 123 to communicate with any of several reagent bottles A (113), B (114), dispense to waste 12, or inject into the Mass Spectrometer 75, either independently (in the discrete eighth rotor position of FIG. 36), or in a combined flow stream with the output of the LC column 96 (in the discrete ninth rotor position of FIG. 37). These valve positions are summarized in TABLE 1 below.

TABLE 1

| Discrete Rotor Position | Output of Second Port 61 | Output of Central port 57 |
| --- | --- | --- |
| 1 (FIG. 29) | To Mass Spec | To reagent A |
| 2 (FIG. 30) | To Mass Spec | To reagent B |
| 3 (FIG. 31) | To Mass Spec | To wash |
| 4 (FIG. 32) | To Mass Spec | To waste |
| 5 (FIG. 33) | n/a | n/a |
| 6 (FIG. 34) | To waste | To waste |
| 7 (FIG. 35) | To waste | Not connected |
| 8 (FIG. 36) | To waste | To Mass Spec |
| 9 (FIG. 37) | To Mass Spec | To Mass Spec |
| 10 (FIG. 38) | n/a | n/a |

In the embodiment of the valve shown in FIGS. 27 and 28, the LC input at the second port 61 is unconnected (dead-ended) in the discrete fifth rotor position of FIG. 33 and in the discrete tenth rotor position of FIG. 38. As mentioned, during operation, if the high-pressure pump 97 was to continue to apply pressure while the valve assembly was in one of these two discrete rotor positions, the high pressure transmitted to the valve assembly might cause valve failure.

With respect to the discrete fifth rotor position of FIG. 33, to prevent failure of this type, the stator face 55 may be modified to include an addition second radial stator groove (not shown). Referring to the discrete fifth rotor position of FIG. 33, an inner end of this second radial stator groove is contained the inner imaginary circle 62, and is in fluid communication with the end of the inner circumferential rotor groove 111 that is opposite the other end thereof that is coincident with the second stator port 61. The opposite outer end of the second radial stator groove is coincident, and in fluid communication, with the ninth stator port 106, at the outer imaginary circle 66. This configuration is similar to that of the continuous fluid communication between the radial stator groove 108 and the fourth stator port 101.

With this modification, in the discrete fifth rotor position of FIG. 33, the extra second stator groove (not shown) now connects the second port 61, through the inner circumferential rotor groove 111, to the ninth stator port 106, and from thence to waste receptacle 112. This embodiment also allows the outer circumferential groove 78 to be flushed which helps minimize contamination when the reagents are switched.

In a similar manner, with respect to the discrete tenth rotor position of FIG. 38, to prevent failure of this type, the rotor face 52 may be modified to include an addition fifth rotor channel 126 (FIG. 39), positioned between the first rotor groove 67 and the first rotor channel 68. Hence, referring to the discrete tenth rotor position of FIG. 39, an inner portion of this fifth rotor channel 126 is contained the inner imaginary circle 62, and is in fluid communication with the second port 61, while an opposite outer portion thereof is contained in, and in fluid communication with, the third stator port 65, at the outer imaginary circle 66.

With this modification, in the discrete tenth rotor position of FIG. 39, the extra fifth rotor groove 126 now continues to connect the output of LC column 96 to the second port 61, via external tubing 125, and to the Mass Spectrometer 75, via stator third port 65. It will be appreciated that these two additions have no impact on fluid flow when the valve is any other position.

It will also be appreciated that the forgoing embodiment is only one of many possible embodiments that can be created using additional stator and rotor grooves. Other fluid channel configurations could be implemented, and would provide different functionality. For example, in the corresponding circumferential and radial rotor and stator grooves and corresponding ports can be switched in that the stator ports located on the outer imaginary circle 66 are moved to the inner imaginary circle 62, and vice versa, while the circumferential rotor and stator grooves are also switched. For example, relocating the inner circumferential rotor groove 111 to the outer imaginary circle 66. Moreover, the size of rotor and stator grooves and channels may be tailored to the application. For example, the first rotor groove 67 connecting the central port 57 with the outer stator ports at radius "R2", could be of a wider diameter so that the aspiration/dispense pump 123 could aspirate and dispense reagents more quickly through it without generating large pressure drops. In contrast, the short radial first-fourth rotor channels 68, 95, 98 and 100, extending from radius "R1" to radius "R2," which communicate the output of the LC column 96 to the mass-spectrometer 75, can be narrower to prevent band-broadening of the peaks being eluted from the LC column.

Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A rotary shear valve assembly comprising:
   a rotor device having a substantially planar rotor face, and
   a stator device having a substantially planar stator face, and defining a first passage extending therethrough that terminates at a central port on said stator face, and at a common central rotational axis of both said rotor face and said stator face, said stator device further defining a second passage extending therethrough that terminates at a second port on said stator face, and radially spaced a radius R1 from said central port, and said stator device further defining a third passage extending therethrough that terminates at a third port on said stator face, radially spaced a radius R2 from said central port and in general linear alignment with said central port and said second port, wherein radius R2 is greater than radius R1;
   said rotor device further having a first rotor groove defined in said rotor face and extending radially outward from said common central rotational axis to a position generally at said radius R2 from said central port, said rotor device being rotatably mounted to said stator device for rotation thereof about said rotational axis in a manner enabling fluid-tight, selective relative rotation between the rotor face and the stator face, at a rotor-stator interface, between two or more discrete rotor positions,
   wherein when said rotor device is in a discrete first rotor position, said first rotor groove is oriented in radial alignment with, and fluidly connects, said central port and said second port with said third port.

2. The rotary shear valve assembly according to claim 1, wherein
   said central port and said second port are input ports for input of respective liquids therethrough, and said third port is an output port for output of said respective liquids therethrough.

3. The rotary shear valve assembly according to claim 1, wherein said central port and said third port are input ports for input of respective liquids therethrough, and said second port is an output port for output of said respective liquids therethrough.

4. The rotary shear valve assembly according to claim 1, wherein
said second port and said third port are input ports for input of respective liquids therethrough, and said central port is an output port for output of said respective liquids therethrough.

5. The rotary shear valve assembly according to claim 2, wherein
said rotor device further includes a first rotor channel defined in said rotor face, extending in a direction radially outward from said common central rotation axis, and commencing from a first radial location generally at said radius R1 from said central port to a second radial location generally at said radius R2 from said central port,
wherein when said rotor device is in a discrete second rotor position, rotationally offset about said central rotational axis from said first rotor position, said first rotor channel is oriented in radial alignment with, and fluidly connects, said second port with said third port.

6. The rotary shear valve assembly according to claim 5, wherein
said rotor device further includes a circumferential rotor groove, having a first arc length, defined in said rotor face, and extending circumferentially about said central rotational axis along an imaginary circle having said radius R2, and
said stator face further includes a circumferential stator groove, having a second arc length, also extending circumferentially around said imaginary circle,
wherein when said rotor device is in a discrete third rotor position, rotationally offset about said central rotational axis from said both said first rotor position and said second rotor position, said first rotor groove is oriented in fluid communication with an end of said circumferential stator groove, and an opposite end of said circumferential stator groove is oriented in fluid communication with an end of said circumferential rotor groove, while an opposite end of said circumferential rotor groove is oriented in fluid communication with said third port, such that said central port is in fluid communication with only said third port.

7. The rotary shear valve assembly according to claim 6, wherein
a sum of the first arc length of the circumferential rotor groove and the second arc length of the circumferential stator groove is at least as long as a third arc length, at radius R2, as the rotor face rotationally turns moving from the first rotor position to the third rotor position.

8. A rotary shear valve assembly comprising:
a rotor device having a substantially planar rotor face, and
a stator device having a substantially planar stator face, said rotor face and said stator face having a common central rotational axis when said rotor device is rotatably mounted to said stator device in a manner enabling fluid-tight, selective relative rotation between the rotor face and the stator face, at a rotor-stator interface, between a plurality of discrete rotor positions, said stator device further defining a second passage extending therethrough that terminates at a second port on said stator face, said second port being contained in a first imaginary circle around said central rotational axis having a radius R1, and said stator device further
defining a third passage extending therethrough that terminates at a third port on said stator face, said third port being contained in a second imaginary circle around said central rotational axis having a radius R2, said third port and said second port are oriented in general linear alignment with said central rotational axis, wherein said stator device defining a first passage extending therethrough that terminates at a central port on said stator face, said central port being positioned coaxial with said common central rotational axis;
said rotor device further having a first rotor channel and a second rotor channel each defined in said rotor face and each extending in a respective direction radially outward from said central rotational axis, each said first rotor channel and said second rotor channel having a respective portion contained in said first imaginary circle and an opposite portion contained in said second imaginary circle,
wherein when said rotor device is in a discrete first rotor position, said first rotor channel is oriented in radial alignment with, and fluidly connects, said second port with said third port, and
wherein when said rotor device is in a discrete second rotor position, immediately adjacent said first rotor position and rotationally offset therefrom about said central rotational axis, said second rotor channel is oriented in radial alignment with, and fluidly connects, said second port with said third port, such that when said rotor device is quickly switched between said first rotor position and said second rotor position, substantially continuous liquid flow from said second port to said third port can be maintained, wherein said rotor device further having an elongated first rotor groove defined in said rotor face and having an end coincident and in fluid communication with said central port at said central rotational axis, said first rotor groove extending radially outward therefrom and terminating at an opposite end thereof contained in said outer imaginary circle,
wherein when said rotor device is in a discrete fourth rotor position, said first rotor groove is oriented in radial alignment with, and fluidly connects, said central port and said second port with said third port.

9. The rotary shear valve assembly according to claim 8, wherein
radius R2 is greater than radius R1,
said first imaginary circle is an inner imaginary circle, and said second imaginary circle is an outer imaginary circle.

10. The rotary shear valve assembly according to claim 9, wherein
said second port is an input port for input of respective liquids therethrough, and said third port is an output port for output of said respective liquids therethrough.

11. The rotary shear valve assembly according to claim 9, wherein
said rotor device further having a third rotor channel defined in said rotor face and extending in a respective direction radially outward from said central rotational axis, said third rotor channel having a inner portion contained in said inner imaginary circle and an opposite outer portion contained in said outer imaginary circle,
wherein when said rotor device is in a discrete third rotor position, immediately adjacent said second rotor position and rotationally offset therefrom about said central rotational axis, said third rotor channel is oriented in radial alignment with, and fluidly connects, said second port with said third port, such that when said rotor device is quickly switched between said second rotor position and said third rotor position, substantially continuous liquid flow from said second port to said third port can be maintained.

* * * * *